United States Patent
Masuda et al.

(10) Patent No.: US 10,390,728 B2
(45) Date of Patent: Aug. 27, 2019

(54) MEDICAL IMAGE DIAGNOSIS APPARATUS

(71) Applicant: Toshiba Medical Systems Corporation, Otawara-shi (JP)

(72) Inventors: Takashi Masuda, Utsunomiya (JP); Shouichi Nakauchi, Nasushiobara (JP); Tomio Nabatame, Otawara (JP); Takashi Koyakumaru, Utsunomiya (JP); Tomoko Suzuki, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 1095 days.

(21) Appl. No.: 14/672,724

(22) Filed: Mar. 30, 2015

(65) Prior Publication Data

US 2015/0272700 A1 Oct. 1, 2015

(30) Foreign Application Priority Data

Mar. 31, 2014 (JP) ................................. 2014-072507

(51) Int. Cl.
*A61B 5/06* (2006.01)
*A61B 17/34* (2006.01)
(Continued)

(52) U.S. Cl.
CPC .......... *A61B 5/061* (2013.01); *A61B 17/3403* (2013.01); *A61B 34/10* (2016.02);
(Continued)

(58) Field of Classification Search
CPC . A61B 19/5244; A61B 17/3403; A61B 5/061; A61B 34/20; A61B 34/10;
(Continued)

(56) References Cited

U.S. PATENT DOCUMENTS

| 4,058,114 A | 11/1977 | Soldner |
| 6,216,029 B1 | 4/2001 | Paltieli |
| (Continued) | | |

FOREIGN PATENT DOCUMENTS

| CN | 1636520 A | 7/2005 |
| CN | 101507616 A | 8/2009 |
| (Continued) | | |

OTHER PUBLICATIONS

Office Action dated Nov. 14, 2017 in Japanese Patent Application No. 2014-072507.

(Continued)

*Primary Examiner* — Bo Joseph Peng
(74) *Attorney, Agent, or Firm* — Oblon, McClelland, Maier & Neustadt, L.L.P.

(57) ABSTRACT

A medical image diagnosis apparatus includes a capturing part configured to photograph a target site of a subject to capture a medical image. The medical image diagnosis apparatus further includes a positional information acquisition unit, a guideline generator, and a display processor. The positional information acquisition unit acquires the positional information of a puncture needle inserted into of the subject. The guideline generator generates a guideline that indicates an insertion route for the puncture needle to reach the target site based on the positional information. The guideline includes scales graduated at predetermined intervals. The display processor displays the guideline with the medical image.

12 Claims, 18 Drawing Sheets

(51) Int. Cl.
*A61B 34/20* (2016.01)
*A61B 34/10* (2016.01)
*A61B 18/14* (2006.01)
*A61B 18/00* (2006.01)
*A61B 90/00* (2016.01)
*A61B 34/00* (2016.01)

(52) U.S. Cl.
CPC .......... *A61B 34/20* (2016.02); *A61B 18/1477* (2013.01); *A61B 2017/3413* (2013.01); *A61B 2018/00595* (2013.01); *A61B 2034/107* (2016.02); *A61B 2034/2051* (2016.02); *A61B 2034/2074* (2016.02); *A61B 2034/252* (2016.02); *A61B 2090/378* (2016.02)

(58) Field of Classification Search
CPC .. A61B 2018/00595; A61B 2017/3413; A61B 18/1477; A61B 2034/2074; A61B 2034/107; A61B 2034/2051; A61B 2090/378; A61B 2034/252
See application file for complete search history.

(56) References Cited

U.S. PATENT DOCUMENTS

| | | | | |
|---|---|---|---|---|
| 2003/0078502 | A1* | 4/2003 | Miyaki | A61B 8/0833 600/461 |
| 2005/0090742 | A1 | 4/2005 | Mine et al. | |
| 2007/0279436 | A1* | 12/2007 | Ng | G06T 19/00 345/624 |
| 2008/0015664 | A1* | 1/2008 | Podhajsky | A61B 18/1477 607/99 |
| 2008/0033240 | A1* | 2/2008 | Hoffman | A61B 90/36 600/109 |
| 2008/0091101 | A1* | 4/2008 | Velusamy | A61B 6/032 600/427 |
| 2009/0204000 | A1 | 8/2009 | Okamura et al. | |
| 2010/0298705 | A1* | 11/2010 | Pelissier | A61B 8/0833 600/443 |
| 2011/0130641 | A1 | 6/2011 | Razzaque et al. | |
| 2011/0245670 | A1 | 10/2011 | Tashiro et al. | |
| 2011/0270087 | A1 | 11/2011 | Yoshida et al. | |
| 2012/0095339 | A1 | 4/2012 | Tashiro | |

FOREIGN PATENT DOCUMENTS

| | | |
|---|---|---|
| CN | 102258385 A | 11/2011 |
| CN | 102551797 A | 7/2012 |
| CN | 103635143 A | 3/2014 |
| JP | 2000-500031 A | 1/2000 |
| JP | 2000-107178 A | 4/2000 |
| JP | 2005-323669 A | 11/2005 |
| JP | 2007-215672 | 8/2007 |
| JP | 2011-206281 A | 10/2011 |
| JP | 2011-229837 A | 11/2011 |
| JP | 2014-28125 A | 2/2014 |

OTHER PUBLICATIONS

Combined Chinese Office Action and Search Report dated Mar. 2, 2017 in Chinese Patent Application No. 201510147923.4 (with English translation of categories of cited documents).

Office Action dated Mar. 22, 2016 in Korean Patent Application No. 10-2015-0044895.

* cited by examiner

MEDICAL IMAGE DIAGNOSIS APPARATUS

CROSS-REFERENCE TO RELATED APPLICATION

This application is based upon and claims the benefit of priority from Japanese Patent Application No. 2014-072507, filed Mar. 31, 2014; the entire contents of which are incorporated herein by reference.

FIELD

Embodiments described herein relate generally to a medical image diagnosis apparatus.

BACKGROUND

A medical image diagnosis apparatus includes a capturing part for photographing a subject to capture medical images thereof. Examples of such medical image diagnosis apparatus include ultrasonic diagnosis apparatuses, X-ray diagnosis apparatuses, X-ray CT (computed tomography) systems, MRI (magnetic resonance imaging) equipment, and the like.

An ultrasonic diagnosis apparatus has an ultrasonic probe, and transmits/receives ultrasonic waves to/from a subject using the ultrasonic probe to obtain echo images as medical images (ultrasound images).

In many clinical practices, a puncture is performed under ultrasound guidance, in which a puncture needle is rendered in an echo image (see, for example, Japanese Unexamined Patent Application Publication No. 2007-215672).

Among puncture techniques is radiofrequency ablation (RFA). In RFA treatment, for example, a puncture needle having an electrode (electrode needle) is used. The puncture needle is inserted into the body of a subject under ultrasound guidance. When the tip of the puncture needle (needle tip) reaches a cauterization object, current called radio wave is conducted to generate heat around the needle, thereby cauterizing the cauterization object. Hereinafter, cauterization of a cauterization object may sometimes be referred to as "real cauterization". Besides, the time when the needle tip reaches the cauterization object may sometimes be referred to as "real cauterization time", and the position of the needle tip at this time may sometimes be referred to as "real cauterization site".

While the puncture needle is being removed or withdrawn after the real cauterization, cauterization is repeatedly performed just a little each time the needle tip has moved a predetermined distance (e.g., about 1 cm) from the real cauterization site. This procedure may sometimes be referred to as "antiproliferative treatment" or simply as "treatment". To cauterize a little bit in the treatment may sometimes be referred to as "little cauterization". In addition, the time when the needle tip has moved the predetermined distance may sometimes be referred to as "little cauterization time", and the position of the needle tip at this time may sometimes be referred to as "little cauterization site". Incidentally, "antiproliferative treatment time" includes "little cauterization time", while "puncture time" includes "real cauterization time" and "antiproliferative treatment time".

In the puncture as described above, it is difficult to know the length of the predetermined distance (e.g., about 1 cm) under ultrasound guidance, and therefore, it is difficult to make a determination as to whether the needle tip has moved the distance. The operator can measure the predetermined distance by measuring a distance along the puncture needle with a distance measurement mechanism and using this as a guide. However, the measurement by a distance measurement mechanism requires considerable care and time, which leads to prolonged work, and thus imposing a heavy burden on patients as well as operators.

DETAILED DESCRIPTION

Figure 1:
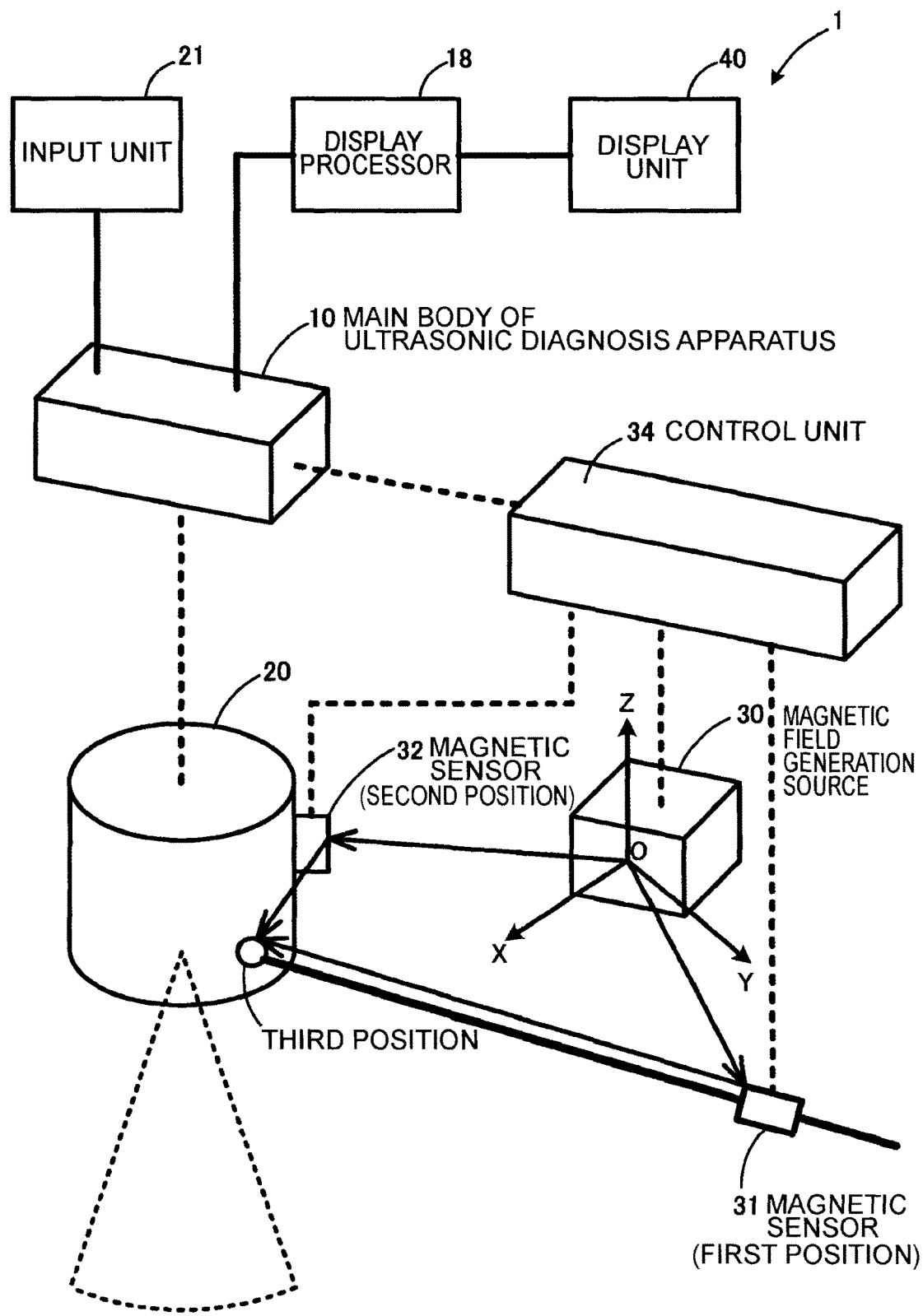
FIG. 1 is a structural block diagram of an ultrasonic diagnosis apparatus according to a first embodiment.

In general, according to one embodiment, a medical image diagnosis apparatus includes a capturing part configured to photograph a target site of a subject to capture a medical image. The medical image diagnosis apparatus further includes a positional information acquisition unit, a guideline generator, and a display processor. The positional information acquisition unit acquires the positional information of a puncture needle inserted into the skin of the subject. The guideline generator generates a guideline that indicates an insertion route for the puncture needle to reach the target site based on the positional information. The guideline includes scales graduated at predetermined intervals. The display processor displays the guideline with the medical image.

(Configuration)

To facilitate the determination of the distance that a puncture needle has moved in the process of removing the needle, according to one embodiment, a medical image diagnosis apparatus is configured to (1) store, in a memory, a scale indicating a predetermined interval corresponding to a predetermined distance by which the puncture needle is moved for little cauterization in antiproliferative treatment, (2) include a location sensor in a position opposite to the tip of the puncture needle, (3) measure the tilt angle of the puncture needle and the position of the sensor with a position measurement system before a puncture or a paracentesis, (4) obtain a needle length that corresponds to a distance from the position of the sensor to the position of the needle tip, (5) obtain the position of the needle tip at real cauterization time based on the obtained needle length, the tilt angle of the puncture needle, and the position of the sensor measured at the real cauterization time, and (6) adjust the scale to the tilt angle of the puncture needle and the position of the needle tip at the real cauterization time, and display it with a medical image.

Regarding (4) "obtain a needle length that corresponds to a distance from the position of the sensor to the position of the needle tip", the needle length may be input by an operator through an input unit 21 (described later); this is referred to as "manual input". The needle length may also be calculated based on the position of the needle tip measured and the position of the sensor; this is referred to as "automatic input".

In addition, "adjust the scale to the position of the needle tip at the real cauterization time" means to "adjust the scale to the reference position of the puncture needle including the needle tip at the real cauterization time". The reference position varies depending on the type of the puncture needle (e.g., mono-polar type, bi-polar type, etc.). The reference position of a mono-polar needle is the position of the needle tip. The reference position of a bi-polar needle is a position a predetermined length away from the position of the needle tip. In the following, the position of the needle tip is described as the reference position.

For the automatic input, a sensor is provided to a part of the medical image diagnosis apparatus other than the puncture needle (hereinafter referred to as "capturing part"). In the capturing part, a position ("third position", described later) is defined that is in a predetermined positional relationship with a position where the sensor is located. The needle tip is adjusted to the position to measure the needle length.

In a first embodiment described below, based on the needle length obtained by the automatic input before a puncture, the tilt angle of the puncture needle, and the position of the sensor (here, a magnetic sensor) measured at the real cauterization time, the position of the needle tip at the real cauterization time is obtained. The scale is then adjusted to the tilt angle of the puncture needle and the position of the needle tip at the real cauterization time, and displayed with a medical image. Incidentally, the position on the puncture needle where the magnetic sensor is located is described as "first position", while the position on the capturing part where the magnetic sensor is provided is described as "second position". Further, a position that is in a predetermined positional relationship with the second position is described as "third position". In the first embodiment, a needle-stick guideline is displayed besides the scale. The needle-stick guideline is a straight line that connects the position of the needle tip at the real cauterization time to the first position, and extends a predetermined length in a direction opposite to the position of the needle tip from the first position. The scale and/or the needle-stick guideline are/is an example of a guide line.

In a second embodiment, a copy of the scale is provided in addition to the scale. The copy of the scale is displayed as being moved along with the position of the needle tip that moves in the process of removing the puncture needle.

In a third embodiment, the scale is displayed by a wearable glass device (eyeglasses-type wearable device) that incorporates a display into an eyeglass.

First Embodiment

In the following, a description is given of a medical image diagnosis apparatus according to the first embodiment with reference to accompanying figures. FIG. 1 is a structural block diagram of the medical image diagnosis apparatus of the first embodiment. In the first embodiment, an ultrasonic diagnosis apparatus is described as an example of the medical image diagnosis apparatus.

FIG. 1 is a structural block diagram of the ultrasonic diagnosis apparatus. As illustrated in FIG. 1, the ultrasonic diagnosis apparatus includes a main body 10, an ultrasonic probe 20, a position measurement system 300, a calculator 100, an insertion position calculator 14, a memory 16, a display processor 18, an intensity calculator 19, the input unit 21, and a display unit 40. The ultrasonic probe 20 is an example of the capturing part. The position measurement system 300 is an example of a measurement unit.

[Mechanism to Obtain Needle Length Before Puncture]

(Position Measurement System 300)

The position measurement system 300 includes a magnetic field generation source (transmitter) 30, magnetic sensors 31 and 32 that detect changes in magnetic field, and a control unit 34 that controls the sensors. The position measurement system 300 performs measurement in response to an instruction from a user. Specifically, the user manually brings the tip of a puncture needle (needle tip) in contact with the third position and provides the instruction by using the input unit 21. The needle length is obtained based on results of the measurement.

The magnetic field generation source 30 is located around the ultrasonic diagnosis apparatus. The location of the magnetic field generation source 30 represents the origin of XYZ coordinates. The magnetic field generation source 30 includes orthogonal 3-axis coils. The magnetic sensors 31 and 32 also include orthogonal 3-axis coils. When the three coils of the magnetic field generation source 30 are sequentially excited, the three coils of the magnetic sensors 31 and 32 sequentially generate electromotive force. The magnetic sensor 31 is provided in the first position on the puncture needle via an adapter (not illustrated). Based on a signal (the electromotive force mentioned above) from the magnetic sensor 31 that has detected a change in the magnetic field of the magnetic field generation source 30, the XYZ coordinates $(x_1, y_1, z_1)$ of the first position and the tilt angles $(\lambda, \mu, \omega)$ of the puncture needle are measured. The tilt angles $\lambda$, $\mu$, and $\omega$ are the angles of the puncture needle with respect to X, Y, and Z axes, respectively.

The magnetic sensor 32 is located in the second position on the ultrasonic probe 20. Based on a signal (the electromotive force mentioned above) from the magnetic sensor 32 that has detected a change in the magnetic field of the magnetic field generation source 30, the XYZ coordinates $(x_2, y_2, z_2)$ of the second position and the tilt angles $(\theta, \delta, \phi)$ of the ultrasonic probe 20 are measured. The second position on the ultrasonic probe 20 represents the origin of UVW coordinates. The tilt angles of the ultrasonic probe 20 refer to the angles of the UVW coordinates with respect to the XYZ coordinates. The UVW coordinates are rotated about U, V, and W axes by angles $\theta$, $\delta$, and $\phi$, respectively, so that they match the XYZ coordinates. The tilt angle of the ultrasonic probe 20 is an example of the tilt angle of the capturing part.

As described above, the position measurement system 300 measures the first position and the tilt angles of the puncture needle, and the second position and the tilt angles of the ultrasonic probe 20. The ultrasonic probe 20 is provided with the third position that is in a predetermined positional relationship with the second position.

The memory 16 stores the positional relationship between the second position and the third position. The positional relationship is defined by the tilt angles $(\alpha, \beta, \gamma)$ of a straight line that connects the second position and the third position and the length $R_1$ of the straight line. The tilt angles $\alpha$, $\beta$, and $\gamma$ are the angles of the straight line with respect to U, V, and W axes of the UVW coordinates, respectively. The memory 16 also stores a scale that indicates a predetermined interval (e.g., 1 cm).

The memory 16 sequentially stores the tilt angle of the puncture needle and the position of the needle tip during a puncture. In addition, the memory 16 stores a predetermined distance by which the position of the needle tip is to be moved at each little cauterization in antiproliferative treatment. The predetermined distance is the same as the predetermined interval (the interval indicated by the scale), and may be, for example, 1 cm. Further, the memory 16 stores the correspondence relationship between the intensity of little cauterization (e.g., current value I) and a distance D from a position where the puncture needle is inserted into the skin to the position of the needle tip at real cauterization time.

[Calculator 100]

Figure 2:
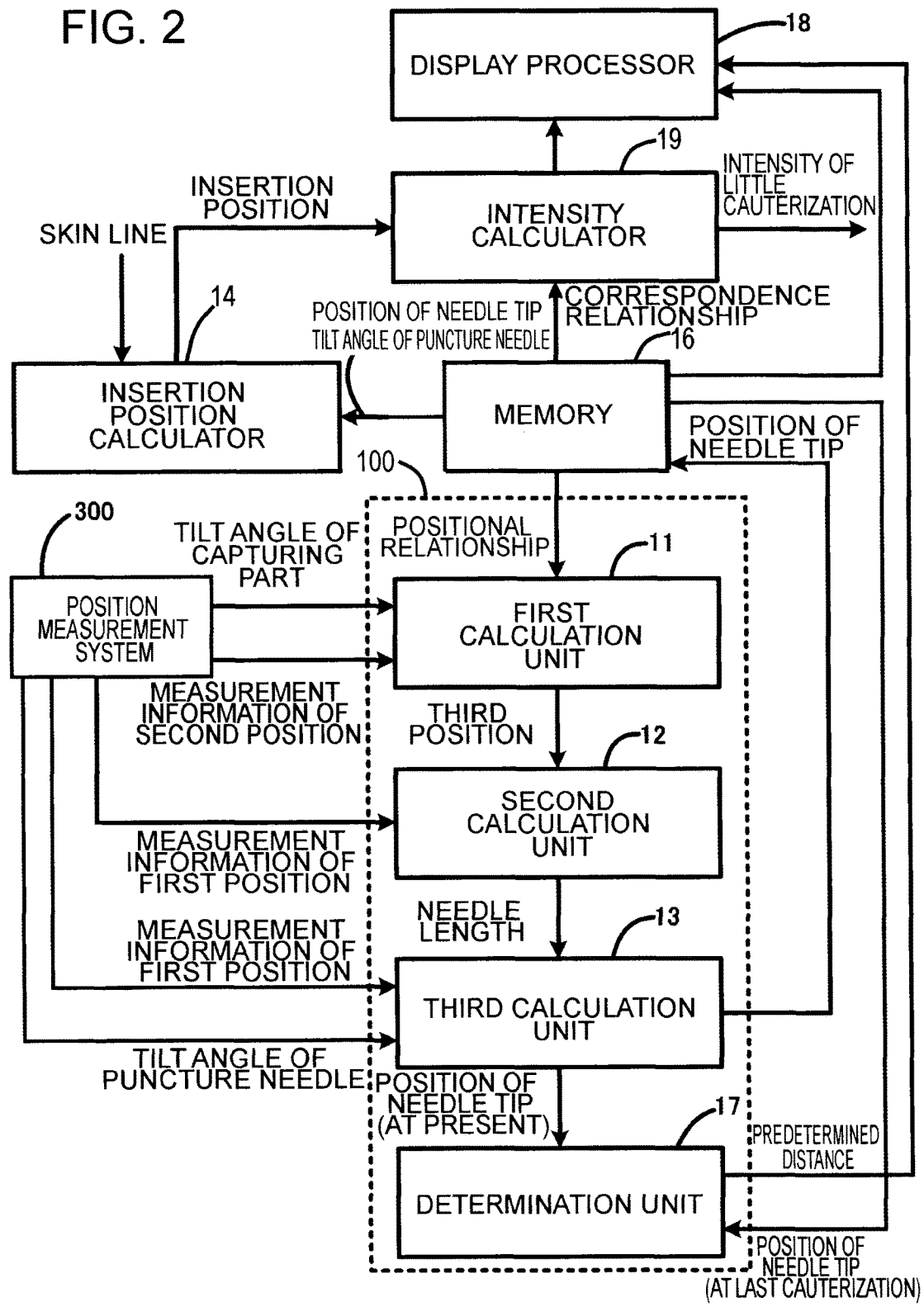
FIG. 2 is a structural block diagram of a calculator and the like of the first embodiment.

The calculator 100 is described next with reference to FIG. 2. FIG. 2 is a structural block diagram of the calculator 100. As illustrated in FIG. 2, the calculator 100 includes a first calculation unit 11, a second calculation unit 12, a third calculation unit 13, and a determination unit 17. The calculator 100 instructs the position measurement system 300 to perform measurements, and obtains measurement values (the XYZ coordinates of the first position, the tilt angle of the puncture needle, the XYZ coordinates of the second position, and the tilt angle of the ultrasonic probe 20) from the position measurement system 300.

(First Calculation Unit 11)

Described below is an example of the first calculation unit 11. The first calculation unit 11 obtains the XYZ coordinates $(x_3, y_3, z_3)$ of the third position by substituting the XYZ coordinates $(x_2, y_2, z_2)$ of the second position where the magnetic sensor 32 is located, the tilt angles $(\alpha, \beta, \gamma)$ of the straight line that connects the second position and the third position, and the length $R_1$ of the straight line into Equation (1) as follows:

[Equation 1]

$$\begin{bmatrix} x_3 \\ y_3 \\ z_3 \end{bmatrix} = \begin{bmatrix} 1 & 0 & 0 \\ 0 & \cos\theta & -\sin\theta \\ 0 & \sin\theta & \cos\theta \end{bmatrix} \begin{bmatrix} \cos\delta & 0 & -\sin\delta \\ 0 & 1 & 0 \\ \sin\delta & 0 & \cos\delta \end{bmatrix} \begin{bmatrix} \cos\phi & -\sin\phi & 0 \\ \sin\phi & \cos\phi & 0 \\ 0 & 0 & 1 \end{bmatrix} \begin{bmatrix} R_1\cos\alpha \\ R_1\cos\beta \\ R_1\cos\gamma \end{bmatrix} + \begin{bmatrix} x_2 \\ y_2 \\ z_2 \end{bmatrix} \quad (1)$$

where $\theta$, $\delta$, and $\phi$ are the rotation angles of the UVW coordinates that are rotated about the U, V, and W axes, respectively, so that they match the XYZ coordinates (the tilt angles of the capturing part).

(Second Calculation Unit 12)

Described below is an example of the second calculation unit 12. The second calculation unit 12 obtains a needle length L that corresponds to a distance from the tip of the puncture needle to a second measurement object by substituting the three-dimensional coordinates $(x_3, y_3, z_3)$ of the third position obtained and the three-dimensional coordinates $(x_1, y_1, z_1)$ of the first position measured into Equation (2) as follows:

[Equation 2]

$$L = ((x_3-x_1)^2 + (y_3-y_1)^2 + (z_3-z_1)^2)^{1/2} \quad (2)$$

As described above, the position measurement system 300 performs measurements when the needle tip is brought in contact with the third position. The needle length L is obtained based on the measurement results.

[Mechanism to Obtain Needle Tip Position for Puncture]

(Third Calculation Unit 13)

The third calculation unit 13 and the position measurement system 300 are used to obtain the position of the needle tip.

Described below is an example of the third calculation unit 13. The needle length L is obtained before a puncture. Next, for the puncture, the needle tip is separated from the third position, and inserted into the body of a subject. Thus, the needle tip reaches a cauterization object. Then, the cauterization object is cauterized (real cauterization). After that, in the process of withdrawal of the puncture needle, antiproliferative treatment that involves repetitive little cauterization is performed. During the puncture, i.e., from when the puncture needle is inserted through the cauterization of the cauterization object until the end of the antiproliferative treatment, the position measurement system 300 measures the XYZ coordinates of the first position and the tilt angle of the puncture needle in the same manner as to obtain the first position for obtaining the needle length L.

The third calculation unit 13 obtains the position $(x_4, y_4, z_4)$ of the needle tip by substituting the needle length L, the tilt angles $\lambda$, $\mu$, $\omega$ of the puncture needle with respect to the X, Y, and Z axes, and the XYZ coordinates $(x_{11}, y_{11}, z_{11})$ of the first position measured by the position measurement system 300 during the puncture into Equation (3) as follows:

[Equation 3]

$$\begin{bmatrix} x_4 \\ y_4 \\ z_4 \end{bmatrix} = \begin{bmatrix} L\cos\lambda \\ L\cos\mu \\ L\cos\omega \end{bmatrix} + \begin{bmatrix} x_{11} \\ y_{11} \\ z_{11} \end{bmatrix} \quad (3)$$

[Display Processor 18]

The display processor 18 includes drawing software, and continuously executes it during the puncture. Using the XYZ coordinates ($x_{11}$, $y_{11}$, $z_{11}$) of the first position, the tilt angles ($\lambda$, $\mu$, $\omega$) of the puncture needle, the needle length L, and the position of the needle tip during the puncture obtained from a function represented by Equation (3), the display processor 18 obtains a needle-stick guideline during the puncture. The needle-stick guideline is a straight line that connects the position of the needle tip to the first position, and extends a predetermined length from the first position in a direction opposite to the position of the needle tip. Thus, the display processor 18 displays an image of the needle-stick guideline during the puncture on the display unit 40 such that it is superimposed on an echo image captured by the capturing part. The position of the tip of the needle-stick guideline during the puncture corresponds to the position ($x_4$, $y_4$, $z_4$) of the needle tip calculated by the third calculation unit 13.

Figure 3:
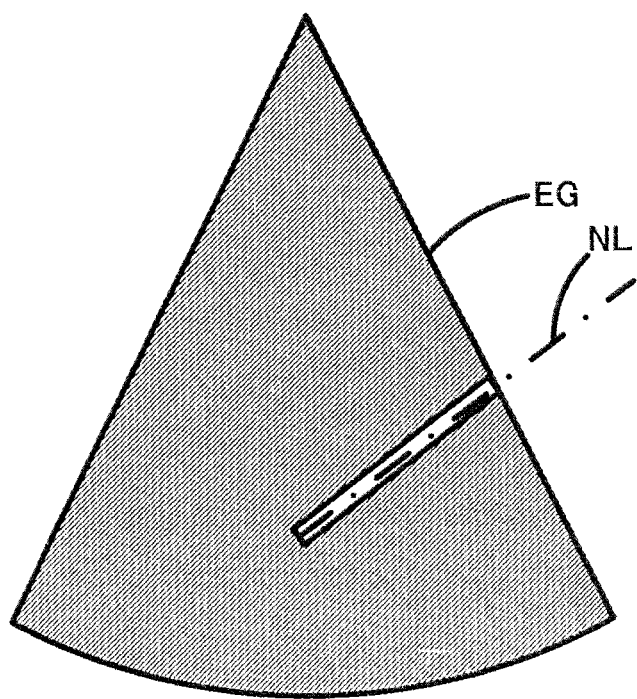
FIG. 3 is a schematic view of an example of a needle-stick guideline at real cauterization time displayed being superimposed on an echo image in the first embodiment.

FIG. 3 is a schematic view of a needle-stick guideline NL at real cauterization time displayed being superimposed on an echo image EG captured by the capturing part. In FIG. 3, an image of the puncture needle drawn in the echo image EG is indicated by a white portion, while the needle-stick guideline NL superimposed on the echo image EG is indicated by an alternate long and short dash line. The display processor 18 displays, on the display unit 40, the needle-stick guideline NL superimposed on the echo image EG. This enables the operator to visually check whether the puncture needle is inserted into a cauterization object with ease and accuracy.

After real cauterization and before the start of antiproliferative treatment, the display processor 18 executes the drawing software in response to operator's operation on the input unit 21 or information as to the completion of the real cauterization. The scale indicating a predetermined interval is retrieved from the memory 16. The display processor 18 displays the scale on the display unit 40 such that it is superimposed on the eco image captured by the capturing part. The scale is adjusted to a real cauterization site obtained when the puncture needle reaches a cauterization object and the tilt angle of the puncture needle at real cauterization time measured when the puncture needle reaches the cauterization object.

Figure 4:
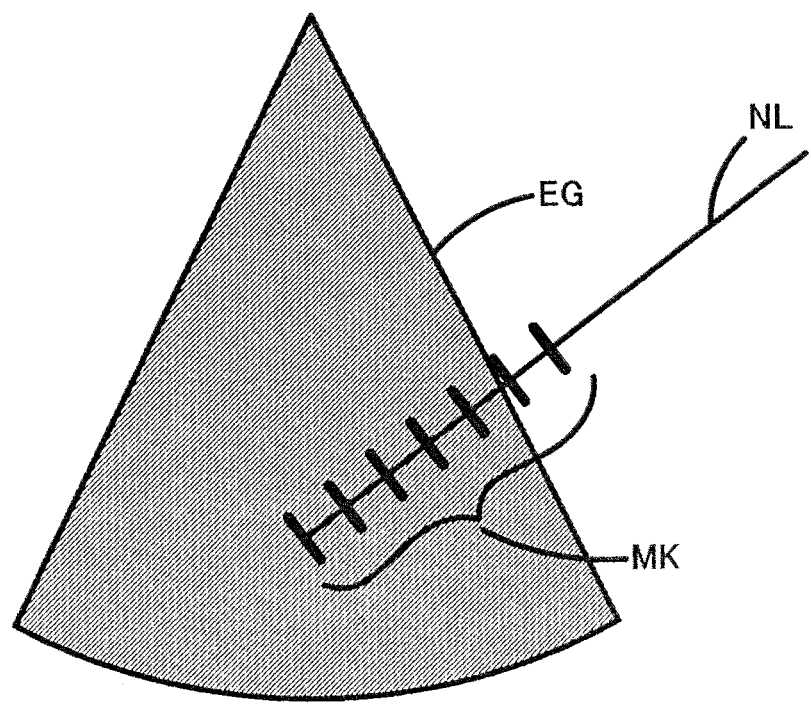
FIG. 4 is a schematic view of an example of a scale at real cauterization time, which is adjusted to the tilt angle of a puncture needle and the position of its needle tip, in the first embodiment.

FIG. 4 is a schematic view of an example of the scale which is adjusted to the tilt angle of the puncture needle and the position of the needle tip at real cauterization time. As illustrated in FIG. 4, the scale includes marks MK that are placed on a plurality of positions provided at predetermined intervals (e.g., 1 cm). The marks MK are formed of lines each having a predetermined width. While the scale is being displayed superimposed on the echo image, the echo image moves on the display along with the movement of the ultrasonic probe 20. Accordingly, if the scale is fixed and stays still on the display, the puncture needle in the echo image shifts from the scale. However, because of the predetermined width of the marks MK, the puncture needle in the echo image does not deviate from the lines of the marks MK of the scale and is kept intersecting with the lines. Thus, the position of the needle tip with respect to the scale can be visually checked without any trouble. There may be, for example, seven marks, and the number of the marked positions is determined in advance. Here, the number of the positions is determined as seven because the predetermined maximum distance from the skin of a subject to the position of the needle tip when the puncture needle reaches a cauterization object is 6 cm (=(7−1) positions×1 cm/position). An example of the marks MK is scale marks.

The display processor 18 adjusts the one end position of the plurality of positions to the real cauterization site, thereby adjusting the scale to the position of the needle tip. With this, a mark MK placed on the one end position is located on the position of the needle tip. The display processor 18 also adjusts the direction of the positions to the tilt angle of the puncture needle at the real cauterization time, thereby adjusting the scale to the tilt angle. As a result, the positions (and marks placed thereon) are aligned along the needle-stick guideline NL.

For convenience of description, it is assumed herein that if the positions are numbered with 0 to 7 from one end position, the display processor 18 adjusts the 0th position to the position of the needle tip at the real cauterization time. Thus, each of the 1st to 6th positions is adjusted to a little cauterization site according to operator's operation. When the needle tip is located at the 0th position, real cauterization is performed by operator's operation. While the operator is removing the puncture needle in antiproliferative treatment after the real cauterization, the needle tip is moved in sequence to the 1st to 6th positions to perform little cauterization at each position. This facilitates the antiproliferative treatment.

Figure 5:
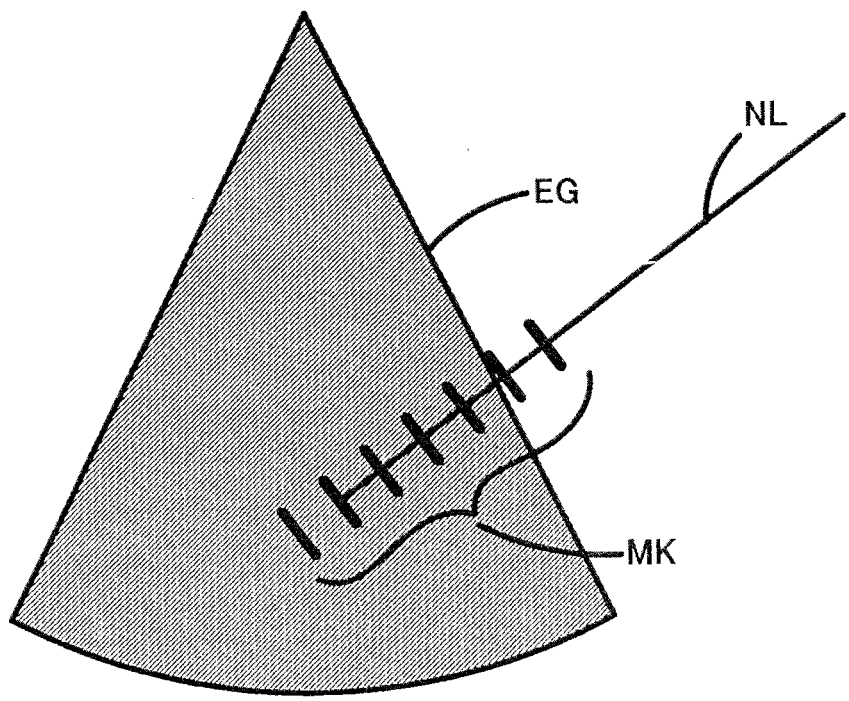
FIG. 5 is a schematic view of an example of the needle-stick guideline whose tip is moved to a first little cauterization site of 0th to 7th sites in the first embodiment.

FIG. 5 is a schematic view of an example of the needle-stick guideline NL whose tip is moved to the 1st position of the 0th to 7th positions. As illustrated in FIG. 5, at the first little cauterization in the antiproliferative treatment, the operator moves the needle tip to the 1st position. In the following little cauterizations, the operator moves the needle tip to the 2nd and the following positions in sequence.

(Example of Scale)

Figure 6:
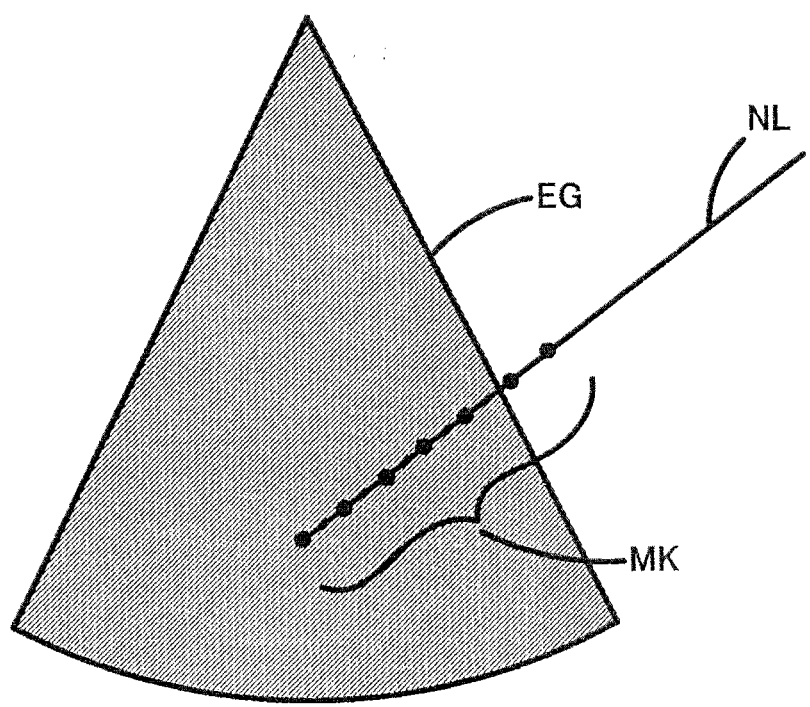
FIG. 6 is a schematic view of an example of the scale, in which marks are placed on a plurality of positions provided at predetermined intervals, in the first embodiment.

FIG. 6 is a schematic view of an example of the scale, in which a mark is placed on a plurality of positions provided at predetermined intervals. The scale may be of any form as long as it indicates the predetermined intervals (e.g., 1 cm). As illustrated in FIG. 6, the scale may have simple dots as the marks MK placed on a plurality of positions provided at predetermined intervals. The display processor 18 displays the scale such that it is adjusted to the tilt angle of the puncture needle at real cauterization time, and one end position of the positions in the scale matches the position of the needle tip at the real cauterization time. Accordingly, a dot placed on the one end position indicates a real cauterization site, and others indicate little cauterization sites.

(Modified Examples of Scale)

Figure 7:
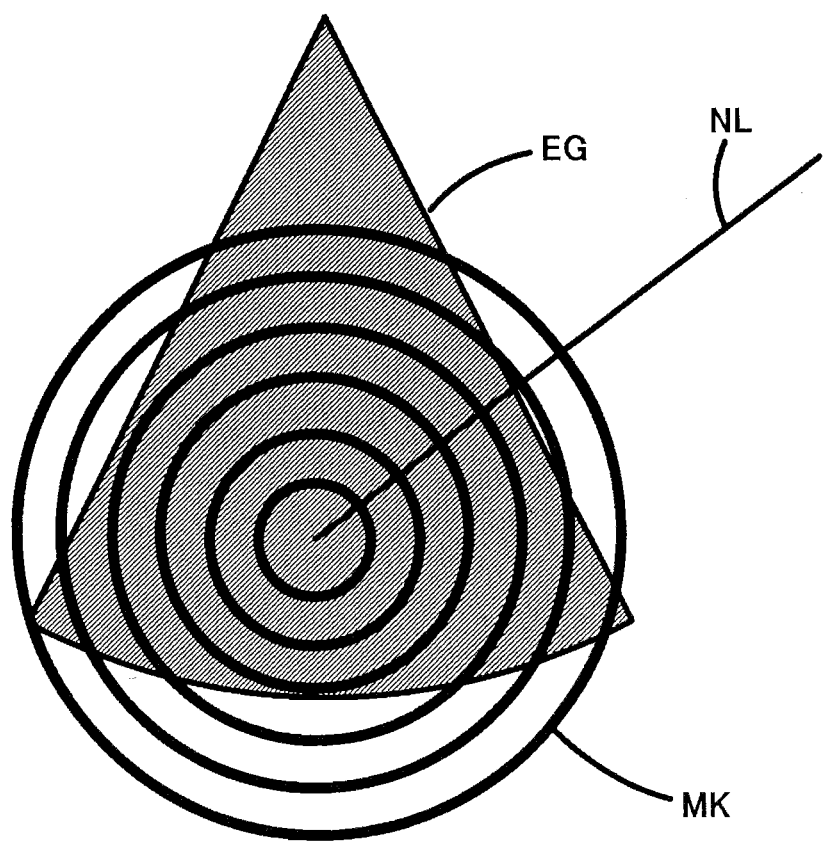
FIG. 7 is a schematic view of a modified example of the scale, which is a scale of concentric circles centered at the position of the needle tip at real cauterization time, in the first embodiment.

FIG. 7 is a schematic view of a modified example of the scale of the embodiment, which is a scale of concentric circles centered at the position of the needle tip at real cauterization site. The display processor 18 may display a scale of concentric circles, whose radii differ by a predetermined amount (e.g., 1 cm), and which are centered at the position of the needle tip at real cauterization time as illustrated in FIG. 7. When the needle tip is being moved in antiproliferative treatment, the position of the needle tip appears to gradually move away from the center of the concentric circles. Thus, the operator can easily check the positional shift of the needle tip.

Figure 8:
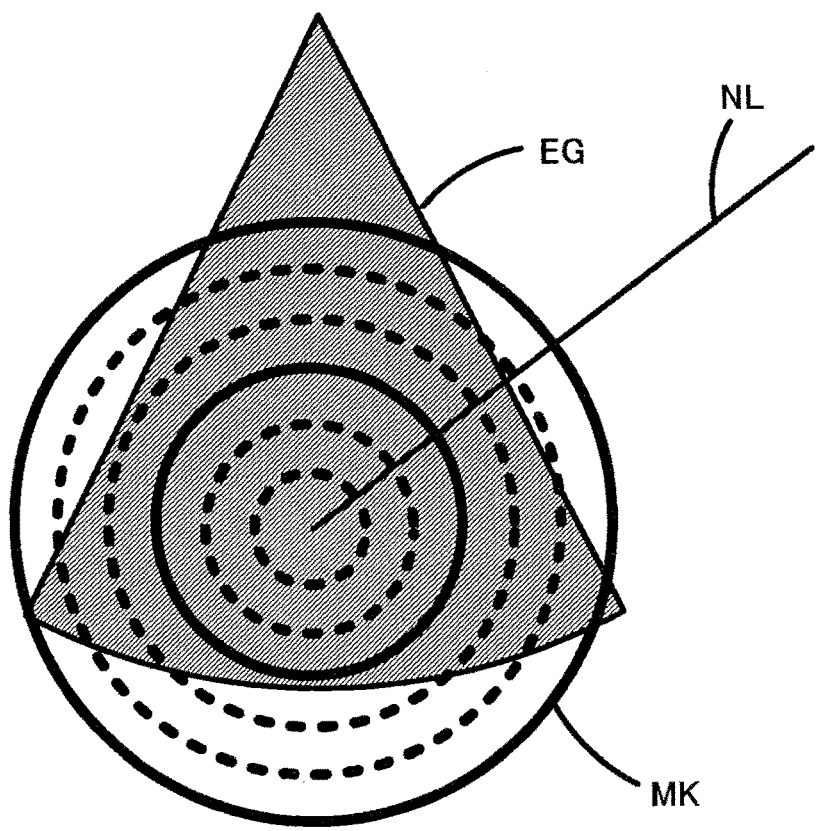
FIG. 8 is a schematic view of another modified example of the scale, which is a scale of concentric circles drawn by different types of lines, in the first embodiment.

FIG. 8 is a schematic view of another modified example of the scale, which is a scale of concentric circles drawn by different types of lines. In antiproliferative treatment, when the position of the needle tip is gradually moving away from the center of the concentric circles, it intersects solid and dashed circles as illustrated in FIG. 8. Hence, this scale further facilitates the checking of the positional shift of the needle tip.

Figure 9:
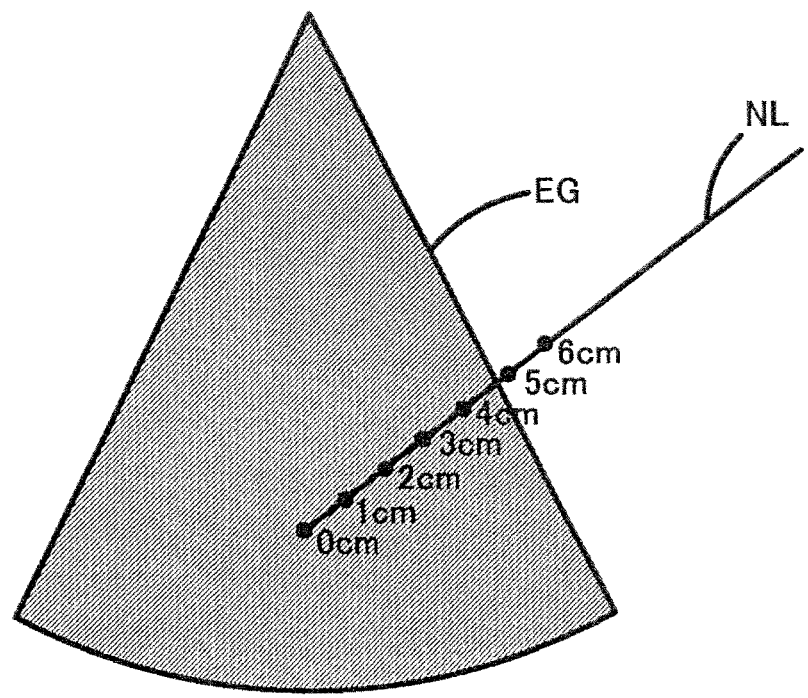
FIG. 9 is a schematic view of still another modified example of the scale, which includes letters indicating a distance from the position of the needle tip that reaches a cauterization object, in the first embodiment.

FIG. 9 is a schematic view of still another modified example of the scale, which includes letters indicating a distance from the position of the needle tip that reaches a cauterization object. Since the scale contains numbers and/or letters as illustrated in FIG. 9, the operator can easily know the distance that the needle tip has moved. Although FIG. 9 provides an example of letters like 0 cm, 1 cm, etc., alphabetical letters such as A, B, etc. may also be used.

Figure 10:
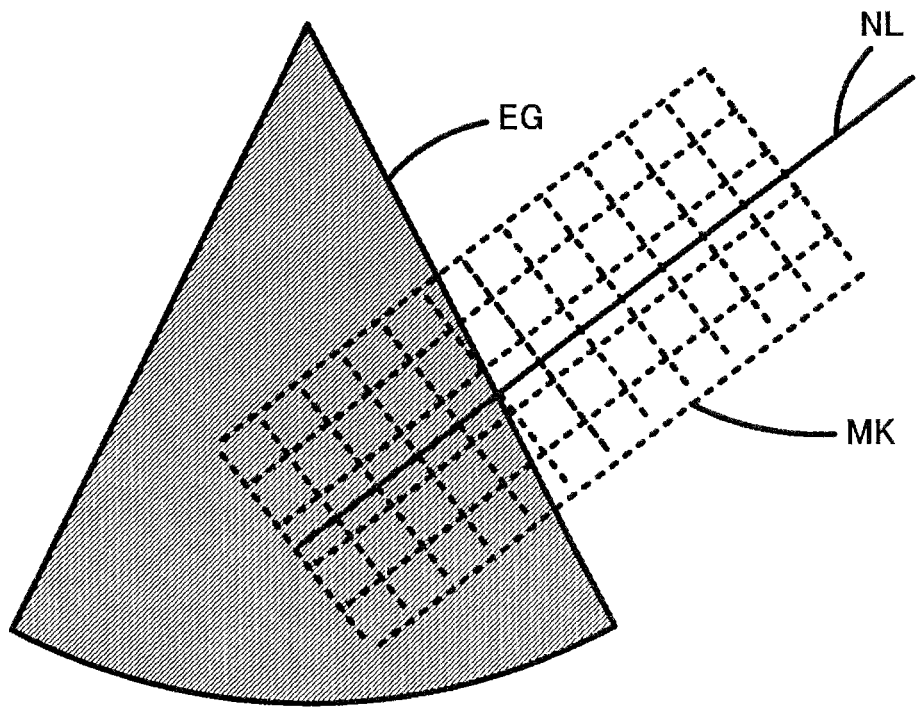
FIG. 10 is a schematic view of still another modified example of the scale having a grid shape in the first embodiment.

FIG. 10 is a schematic view of still another modified example of the scale having a grid shape. While FIG. 10 illustrates a dashed grid, the grid may be drawn by any type of line, and, for example, may be drawn by a solid line. In antiproliferative treatment, when the position of the needle tip is being moved, it intersects the lines of the grid. Thus, the operator can easily check the positional shift of the needle tip.

The above example and modified examples may be used individually or in combination. That is, the display processor 18 may display a combination of two or more of them on the display unit 40.

Among the 0th to 7th positions illustrated in FIGS. 4 and 5, the 0th position is a real cauterization site, the 1st to 4th positions are little cauterization sites, and the 5th and 6th positions are non-cauterization sites where cauterization is not performed (this is determined by the intensity calculator 19 described later). To facilitate antiproliferative treatment, the following may be effective: 1. cauterization sites and non-cauterization sites are distinguishably displayed, 2. further, little cauterization sites are displayed such that whether they have already been cauterized or not is distinguishable, 3. still further, the little cauterization sites are displayed such that whether little cauterization is applicable or not is visually recognizable. To recognizably display cauterization sites and non-cauterization sites, the number of little cauterizations required in antiproliferative treatment is calculated by dividing a distance from a position where the puncture needle is inserted into the skin to the position of the needle tip at real cauterization time by the predetermined distance.

Before the start of antiproliferative treatment, the display processor 18 displays marks that represent the 1st to 4th little cauterization sites in the first mode (indicating that although the position can be cauterized, cauterization is yet to be performed). Having informed of the completion of little cauterization, the display processor 18 switches the first mode to the second mode (indicating that the position has already cauterized) to display a mark representing a little cauterization site where the little cauterization is completed.

Figure 11:
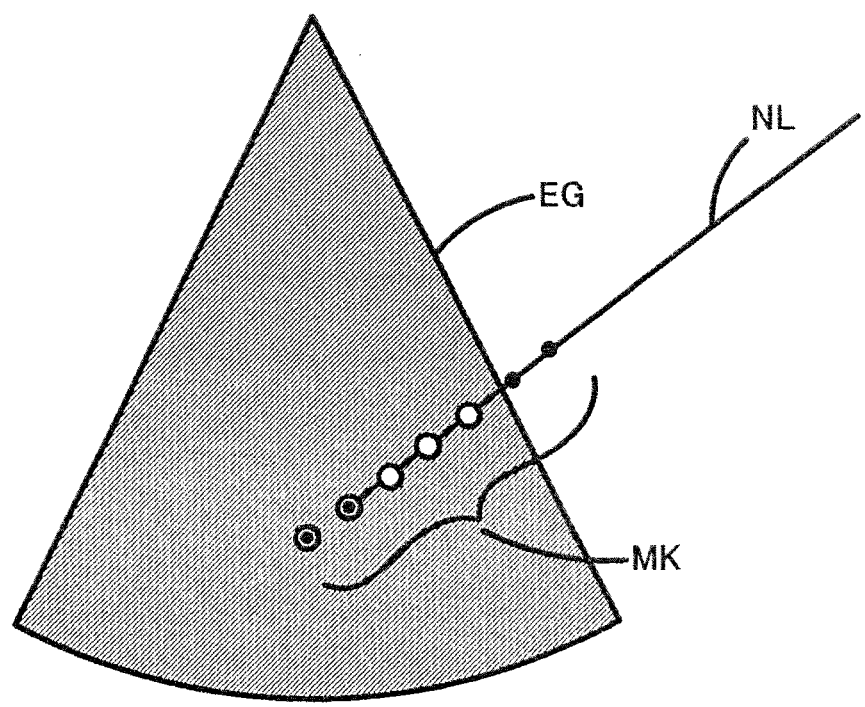
FIG. 11 is a schematic view for explaining an example of the first mode representing non-cauterized state and the second mode representing little-cauterized state in the first embodiment.

FIG. 11 is a schematic view for explaining an example of the first mode representing non-cauterized state and the second mode representing little-cauterized state. Incidentally, the display processor 18 receives cauterization completion information and the number of completed cauterizations from the determination unit 17. When receiving the number of completed cauterizations "1", the display processor 18 switches the display mode of the mark MK placed on the 1st position corresponding to the number "1" to the second mode as illustrated in FIG. 11. In the example of FIG. 11, positions are represented by single-circle (○) in the first mode, and by double-circle (◉) in the second mode.

(Insertion Position Calculator 14)

As described above, to calculate the number of little cauterizations required in antiproliferative treatment, it is necessary to obtain a position where the puncture needle is inserted into the skin (insertion position). To obtain the insertion position, before the antiproliferative treatment, the line of the skin of a subject is extracted based on the pixel value of a medical image (here, an echo image) captured by the capturing part. The insertion position calculator 14 obtains the insertion position based on the extracted line of the skin and the needle-stick guideline NL at real cauterization time, and stores it in the memory 16.

(Intensity Calculator 19)

Although the intensity of little cauterization (e.g., current value) may be constant, if a little cauterization site is near the skin surface, the heat of cauterization is conducted to the skin, and the subject may feel uncomfortable from the heat. Therefore, when a little cauterization site is near the skin surface, the intensity of little cauterization may be reduced so that the subject does not feel the heat. Thus, the intensity calculator 19 retrieves the insertion position and the current position of the needle tip from the memory 16, and calculates a distance D1 from the insertion position to the current position of the needle tip. In addition, referring to the correspondence relationship retrieved from the memory 16, the intensity calculator 19 calculates the intensity of little cauterization based on the distance D1.

In an example of the correspondence relationship, the intensity of little cauterization is reduced when the distance D1 is a predetermined value or less, as compared to that when the distance D1 exceeds the predetermined value. The intensity may be reduced to a fixed low value, or it may be gradually reduced to a lower value. Besides, assuming that the number of little cauterizations required for antiproliferative treatment is N, the intensity of little cauterization may be reduced in the (k+1)th to Nth cauterizations as compared to the 1st to kth ($2 \leq k \leq (N-1)$) cauterizations. The intensity may be reduced to a fixed low value, or it may be gradually reduced to a lower value.

To obtain the number N of little cauterizations, during antiproliferative treatment, the intensity calculator 19 obtains a distance D ($\geq$D1) between the position of the needle tip at real cauterization time obtained by the third calculation unit 13 and the insertion position obtained by the insertion position calculator 14, and stores it in the memory 16. The intensity calculator 19 then divides the distance D by a predetermined distance that is a travel distance of the needle tip between little cauterizations in the antiproliferative treatment to obtain the number N of little cauterizations required for the antiproliferative treatment. The intensity calculator 19 stores the obtained number N in the memory 16.

(Determination Unit 17)

In antiproliferative treatment, when moving the position of the needle tip by a predetermined distance (e.g., 1 cm) for each little cauterization, the operator refers to the scale indicating a predetermined interval (the same value as the predetermined distance, e.g., 1 cm) displayed with a medical image. Thus, the operator can easily perform the antiproliferative treatment.

To further facilitate antiproliferative treatment, during the antiproliferative treatment, the determination unit 17 obtains a distance between the current position of the needle tip and the position of the needle tip at the last little cauterization time obtained by the third calculation unit 13, and determines whether the obtained distance exceeds the predetermined distance (stored in the memory 16). Based on the determination result, the display processor 18 provides display on the display unit 40 to make it recognizable whether the current position of the needle tip reaches a little cauterization site, and also if the little cauterization site has already been cauterized.

[Operation]

Figure 12:
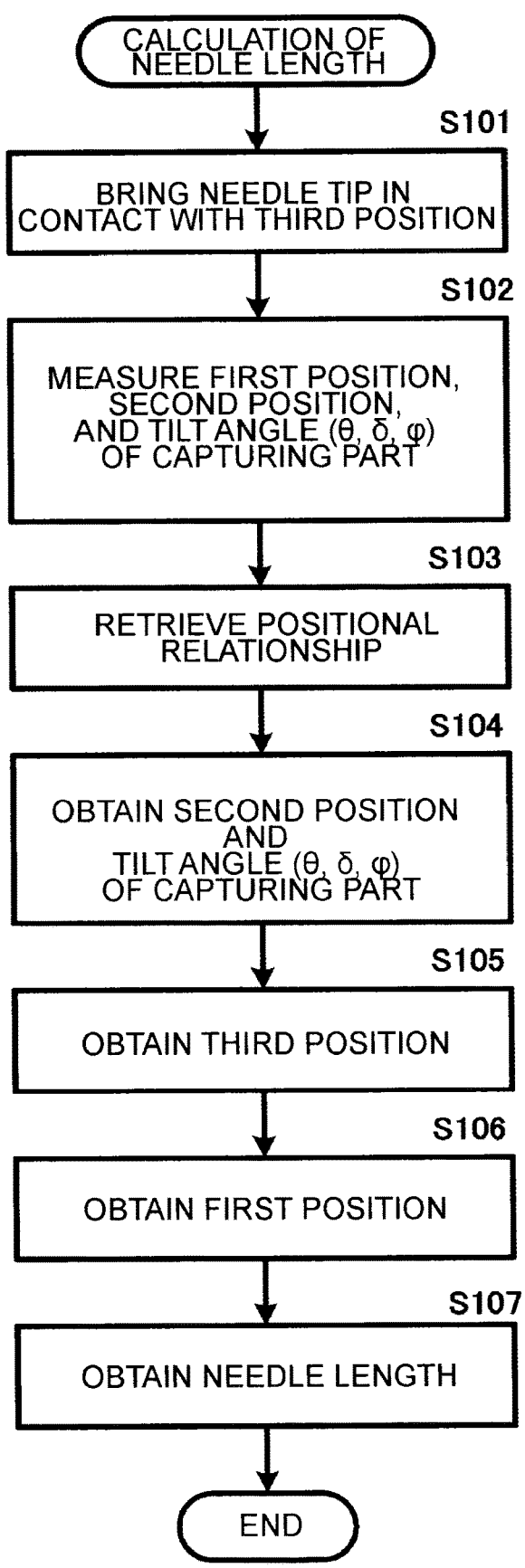
FIG. 12 is a flowchart of the operation of calculating a needle length in the first embodiment.
Figure 13:
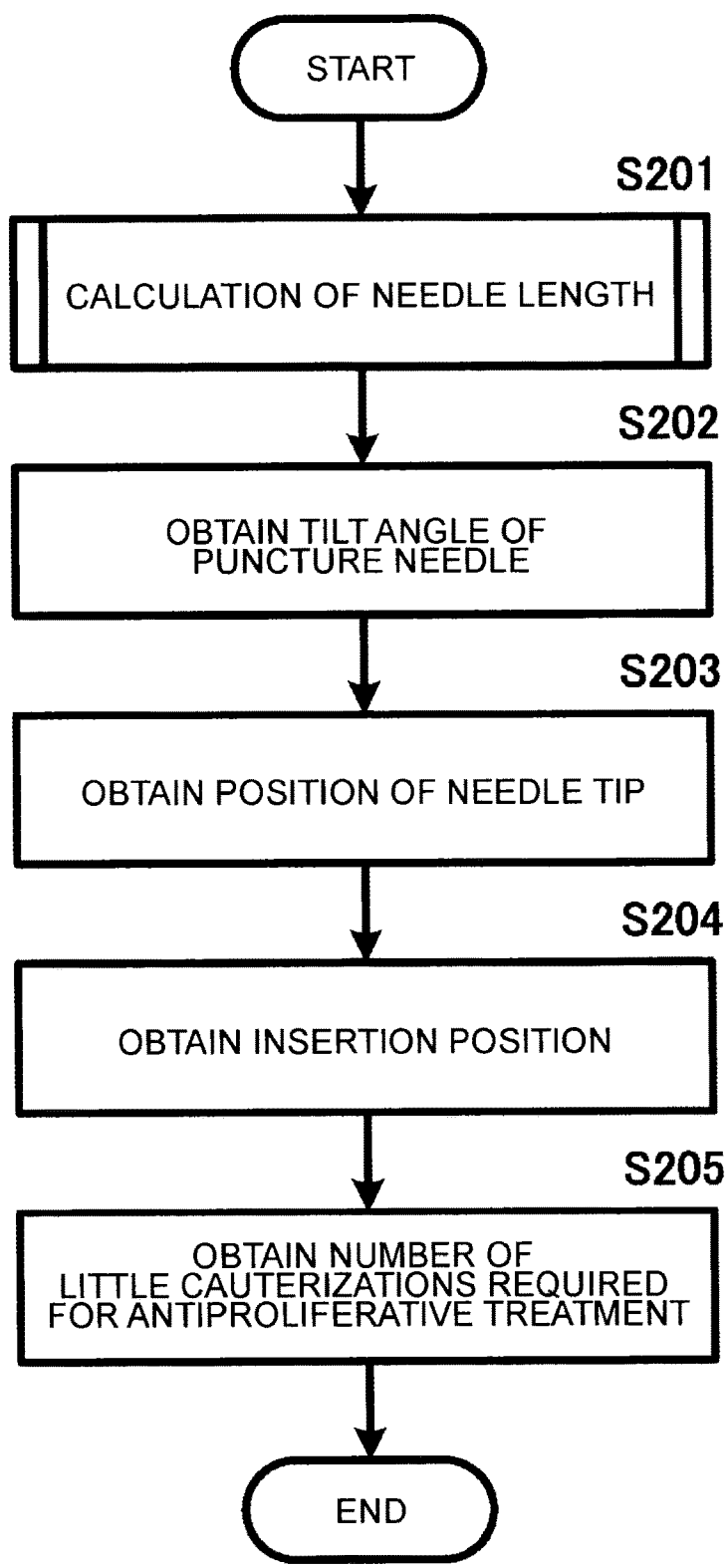
FIG. 13 is a flowchart of the operation for obtaining the position of the needle tip and the like after the calculation of the needle length in the first embodiment.

In the following, with reference to FIGS. 12 and 13, a description is given of the operation for obtaining a needle length, and also the position of the needle tip and the like during a puncture. FIG. 12 is a flowchart of the operation of calculating a needle length.

As illustrated in FIG. 12, first, the needle tip is brought in contact with the third position (step S101). At this time, the operator can easily bring the needle tip in contact with the third position while holding the ultrasonic probe 20 by one hand and the puncture needle by the other and bringing them close to each other. Next, the position measurement system 300 measures the first position, the second position, and the tilt angle of the ultrasonic probe 20 as a capturing part (step S102).

The measurements of the first position, the second position, and the tilt angle of the ultrasonic probe 20 may be performed in arbitrary order. After the measurements, the needle tip may be separated from the third position, and the tilt angle of the ultrasonic probe 20 may be changed.

The first calculation unit 11 retrieves from the memory 16 the positional relationship between the second position and the third position (step S103). The first calculation unit 11 then obtains the second position and the tilt angle of the ultrasonic probe 20 (step S104).

After that, the first calculation unit 11 obtains the third position by substituting the positional relationship of the third position with respect to the second position, the second position, and the tilt angle of the ultrasonic probe 20 into Equation (1) described above (step S105).

The second calculation unit 12 obtains the first position (step S106). Thereafter, the second calculation unit 12 obtains a needle length by substituting the second position and the third position into Equation (2) as above (step S107).

In the calculation of the needle length before a puncture, the needle tip is brought in contact with the third position. Then, the position measurement system 300 measures the first position, the second position, and the tilt angle of the ultrasonic probe 20. Thus, the needle length is obtained based on the measurement results. In the puncture, the needle tip is separated from the third position. During the puncture, the position measurement system 300 measures the first position and the tilt angle of the puncture needle, and the position of the needle tip is obtained based on the measurement results. Accordingly, the display processor 18 displays the scale and the needle-stick guideline on the display unit 40.

In the following, a description is given of the operation for obtaining the position of the needle tip after the calculation of the needle length and the like with reference to FIG. 13. FIG. 13 is a flowchart of the operation for obtaining the position of the needle tip after the calculation of the needle length. As illustrated in FIG. 13, after the needle length is obtained (step S201), the position measurement system 300 measures the XYZ coordinates of the first position and the tilt angle of the puncture needle (step S202). The calculator 100 stores the tilt angle of the puncture needle measured during the puncture in the memory 16 each time it is obtained.

The third calculation unit 13 obtains the position of the needle tip by substituting the needle length, the tilt angle of the puncture needle, and the XYZ coordinates of the first position into Equation (3) as above (step S203). The calculator 100 stores the position of the needle tip obtained during the puncture in the memory 16 each time it is obtained. After that, the insertion position calculator 14 obtains the needle-stick guideline based on the obtained position of the needle tip and the XYZ coordinates of the first position. The insertion position calculator 14 than obtains the insertion position where the puncture needle is inserted into the skin based on the needle-stick guideline and the line of the skin extracted based on the pixel value of a medical image (step S204).

The intensity calculator 19 retrieves the insertion position from the memory 16 to obtain the distance D from the insertion position to the real cauterization site. By dividing the distance D by a predetermined distance, the intensity calculator 19 obtains the number N of little cauterizations required for the antiproliferative treatment (step S205). The calculator 100 stores the number N of required little cauterizations in the memory 16.

Figure 14:
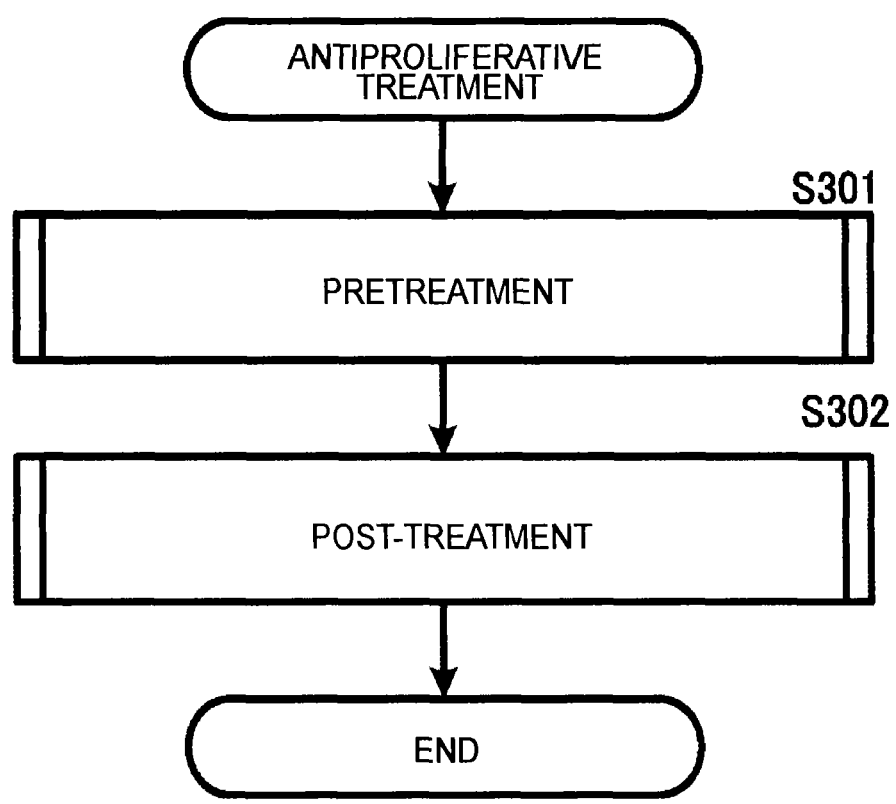
FIG. 14 is a flowchart of antiproliferative treatment of the first embodiment.

In the following, a description is given of the operation of the antiproliferative treatment with reference to FIGS. 14 to 16. FIG. 14 is a flowchart of the antiproliferative treatment of the first embodiment. As illustrated in FIG. 14, the antiproliferative treatment includes pretreatment (step S301) from the receipt of an instruction on the antiproliferative treatment after the real cauterization until the display of the scale, and post-treatment (step S302) from the management of needle-tip movement information through the calculation of little-cauterization intensity until the display of marks, performed after the pretreatment.

Figure 15:
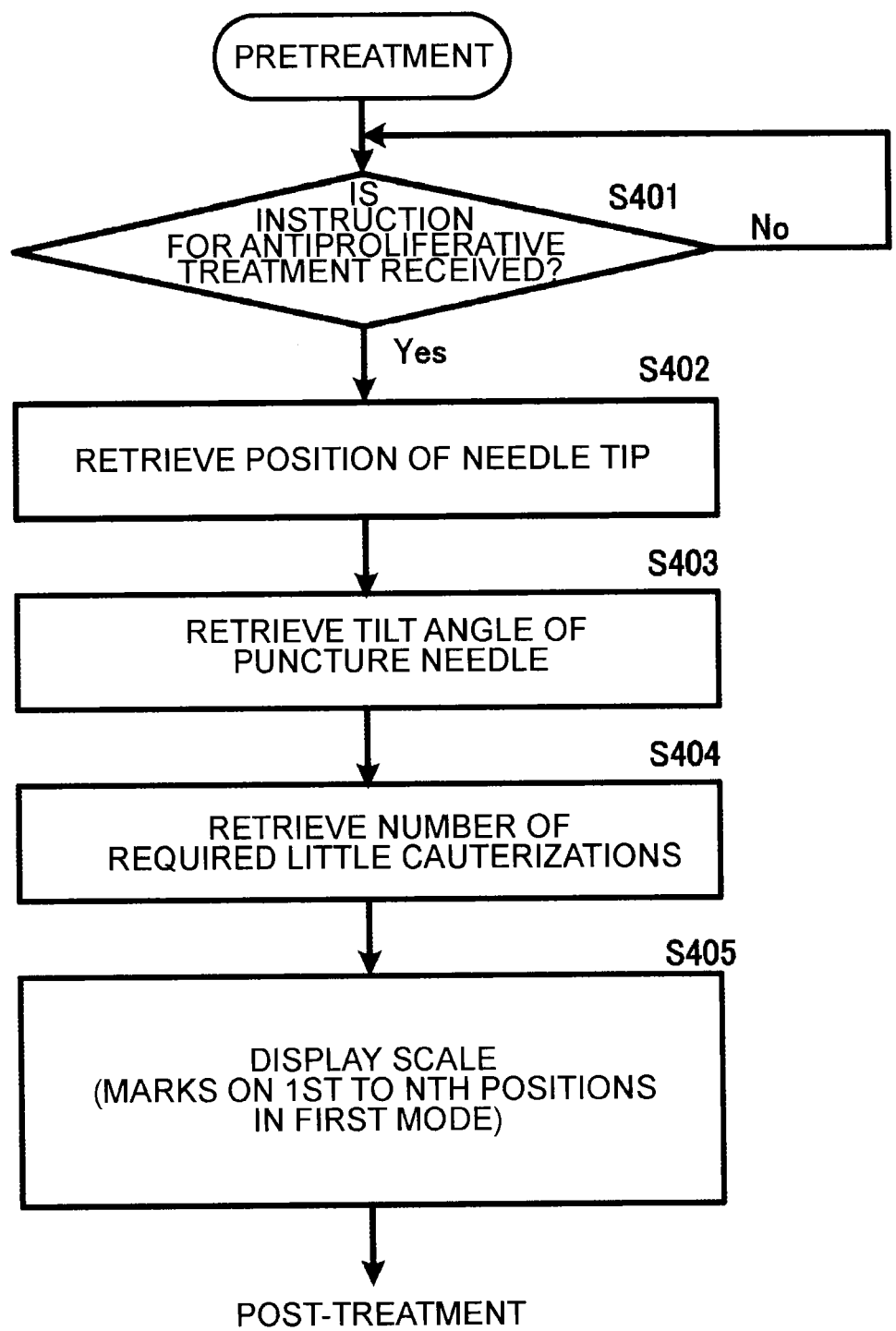
FIG. 15 is a flowchart of pretreatment of the first embodiment.
Figure 16:
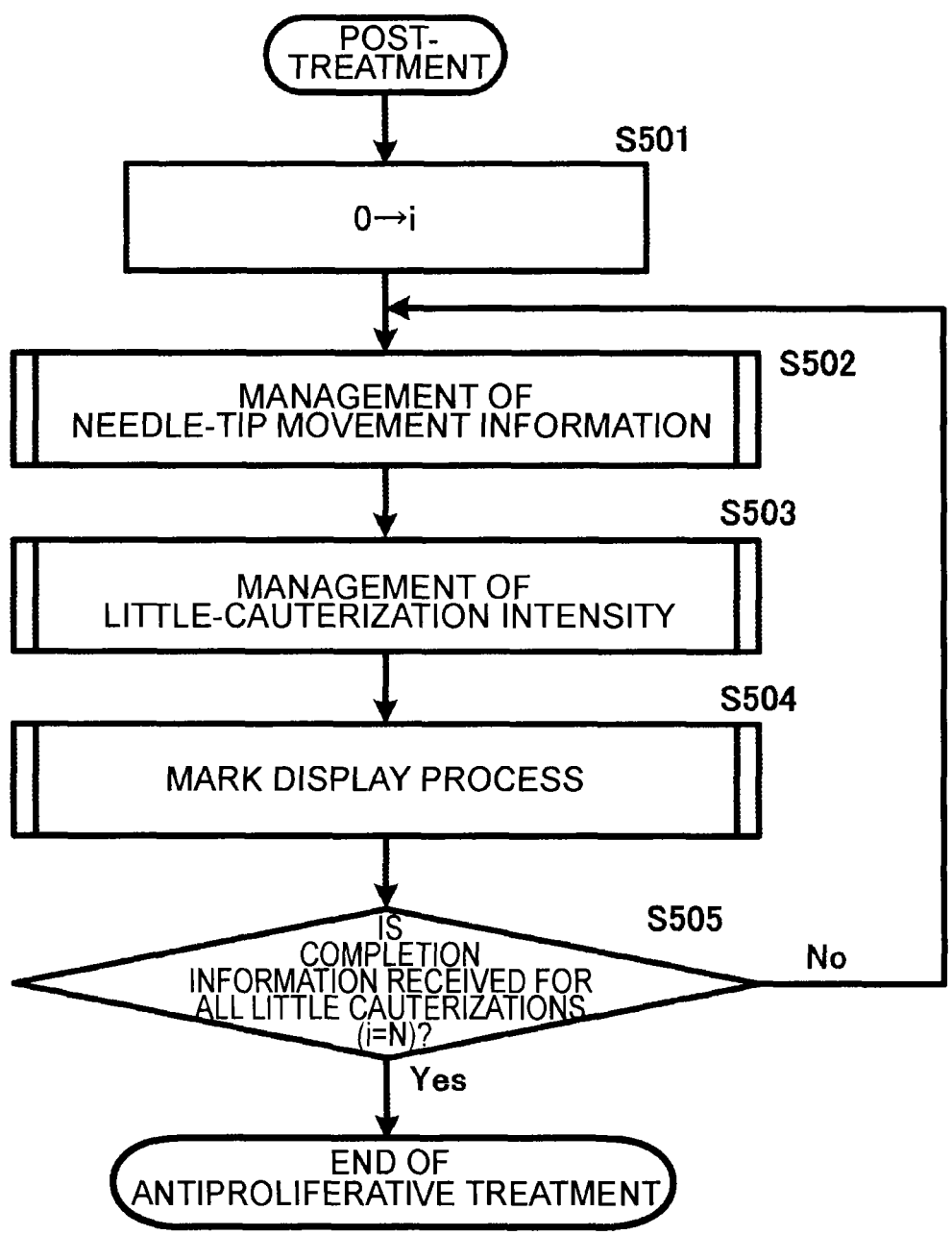
FIG. 16 is a flowchart of post-treatment of the first embodiment.

FIG. 15 is a flowchart of the pretreatment. As illustrated in FIG. 15, first, the calculator 100 determines whether an instruction to perform antiproliferative treatment has been received (step S401). The calculator 100 then retrieves the position of the needle tip at the real cauterization time from the memory 16 (step S402). Next, the calculator 100 retrieves the tilt angle of the puncture needle at the real cauterization time from the memory 16 (step S403). The calculator 100 further retrieves the number N of required little cauterizations from the memory 16 (step S404). Note that the order of steps 402 to 404 is not necessarily as listed above, and they can be performed in arbitrary order.

The display processor 18 displays, with a medical image, the scale such that it matches the tilt angle of the puncture needle and the position of the needle tip at the real cauterization time (step S405). In the scale, marks MK are placed on a plurality of positions (the 0th to 7th positions) provided at predetermined intervals. After real cauterization and before little cauterization, the display processor 18 displays a mark MK placed on the 0th position (real cauterization site) in the second mode (●), and marks MK placed on the 1st to Nth positions (little cauterization sites) in the first mode (○). Thereafter, the post-treatment is performed (step S302 in FIG. 14).

In the following, the post-treatment is described with reference to FIGS. 16 to 19. FIG. 16 is a flowchart of the post-treatment. As illustrated in FIG. 16, 0 is substituted for a variable i (step S501).

The determination unit 17 manages information of the movement of the needle tip (hereinafter, needle-tip movement information) during the antiproliferative treatment (step S502). The intensity calculator 19 manages the intensity of little cauterizations (step S503). The display processor 18 performs the display process of the marks MK (step S504). Then, the determination unit 17 determines whether completion information has been received for all the little cauterizations (step S505). For example, when having received signals informing the completion of cauterization for all the little cauterizations and also information of i=N, the determination unit 17 determines that completion information has been received for all the little cauterizations (Yes in step S505). With this, the antiproliferative treatment is finished. If the determination unit 17 determines that completion information has not yet been received for all the little cauterizations (No in step S505), the process returns to step S502 of managing needle-tip movement information.

Figure 17:
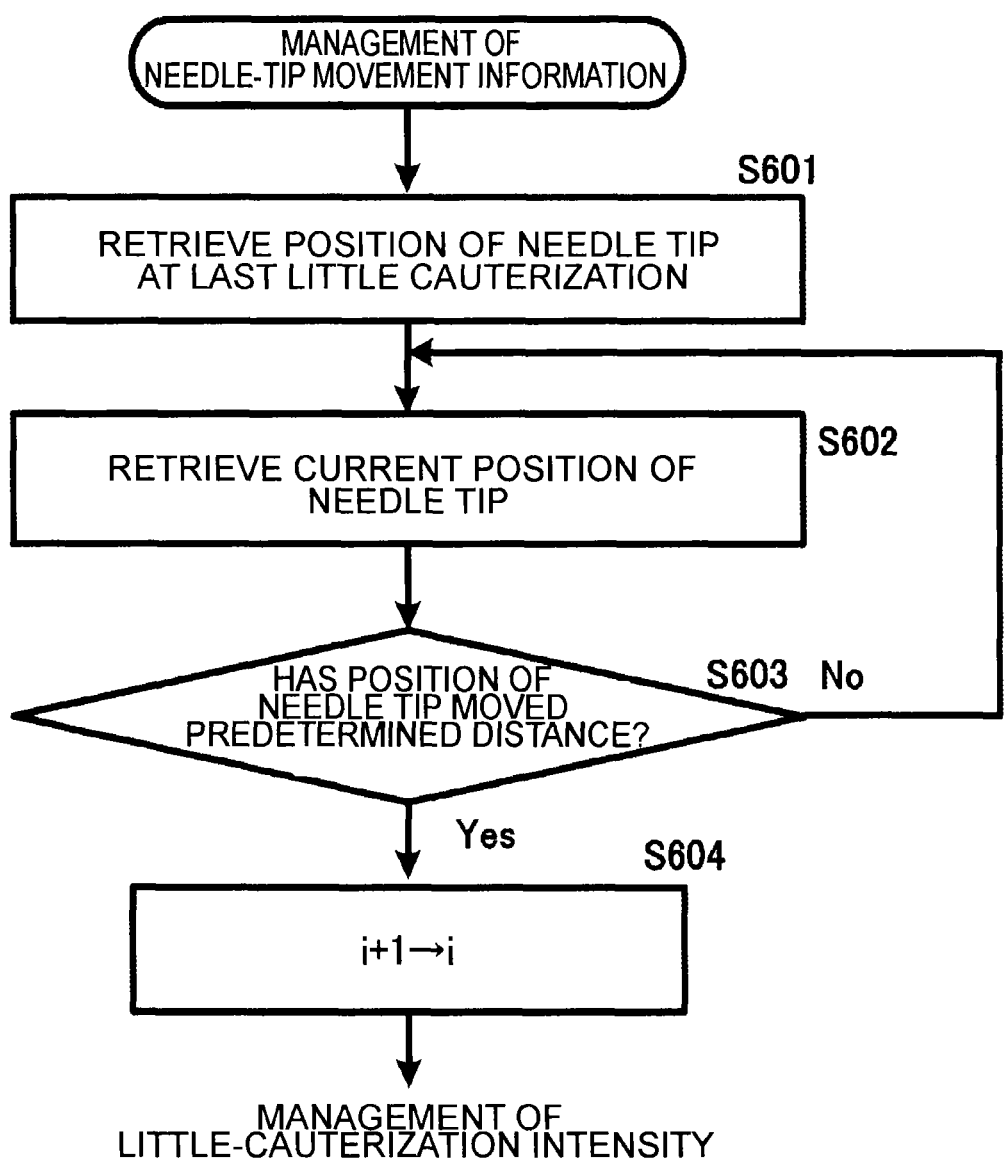
FIG. 17 is a flowchart of the process of managing needle-tip movement information in the first embodiment.

In the following, a description is given of the management of needle-tip movement information with reference to FIG. 17. FIG. 17 is a flowchart of the process of managing needle-tip movement information. As illustrated in FIG. 17, the determination unit 17 retrieves the position of the needle tip at the last little cauterization time from the memory 16 (step S601). In addition, the determination unit 17 retrieves the current position of the needle tip from the memory 16 (step S602). The determination unit 17 then subtracts the current position of the needle tip from the position thereof at the last little cauterization time to compare the obtained value with the predetermined distance. Thereby, the determination unit 17 determines whether the position of the needle tip has moved the predetermined distance (step S603). When the determination unit 17 determines that the position of the needle tip has moved the predetermined distance (Yes in step S603), the variable i is incremented by 1 (step S604). If not (No in step S603), the process returns to step S602 of retrieving the current position of the needle tip from the memory 16.

Figure 18:
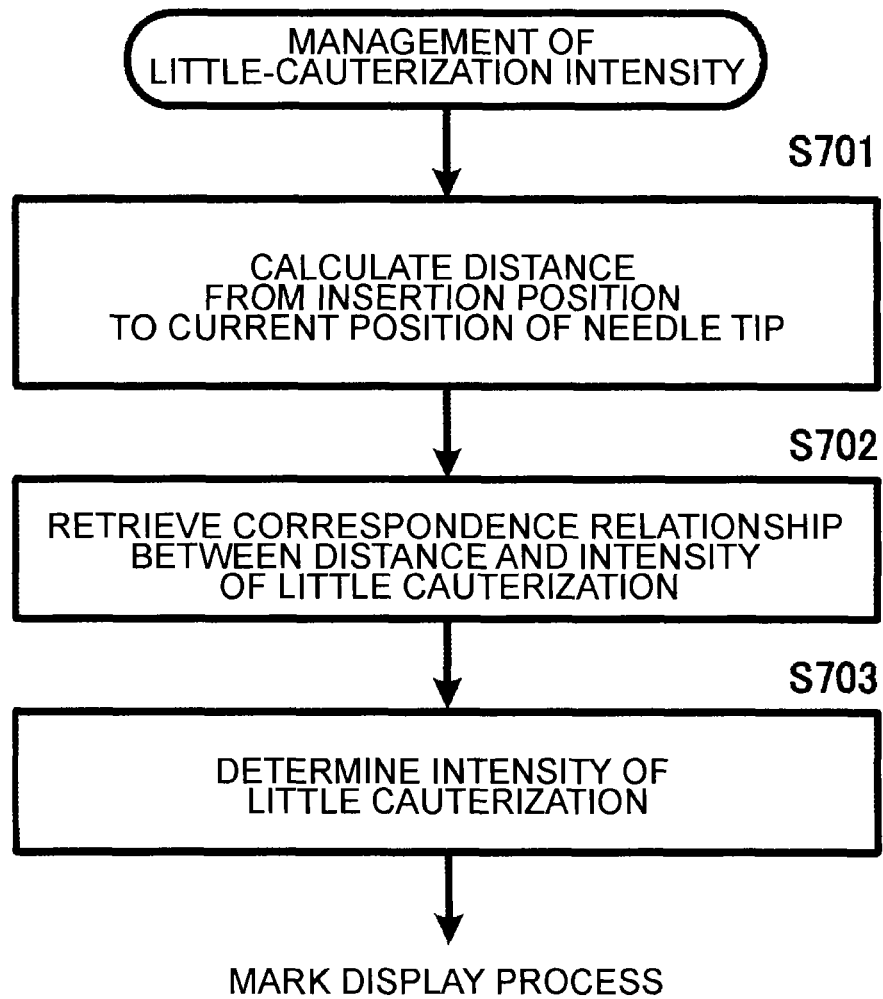
FIG. 18 is a flowchart of the process of managing little-cauterization intensity in the first embodiment.

Next, a description is given of the management of the intensity of little cauterization with reference to FIG. 18. FIG. 18 is a flowchart of the process of managing little-cauterization intensity. As illustrated in FIG. 18, the intensity calculator 19 retrieves from the memory 16 the insertion position where the puncture needle is inserted into the skin as well as the current position of the needle tip. The intensity calculator 19 then calculates a distance D1 from the insertion position to the current position of the needle tip (step S701). Thereafter, the intensity calculator 19 retrieves the correspondence relationship between the distance D1 and the intensity of little cauterization from the memory 16 (step S702). Referring to the correspondence relationship, the intensity calculator 19 determines the intensity of little cauterization based on the distance D1 (step S703).

Figure 19:
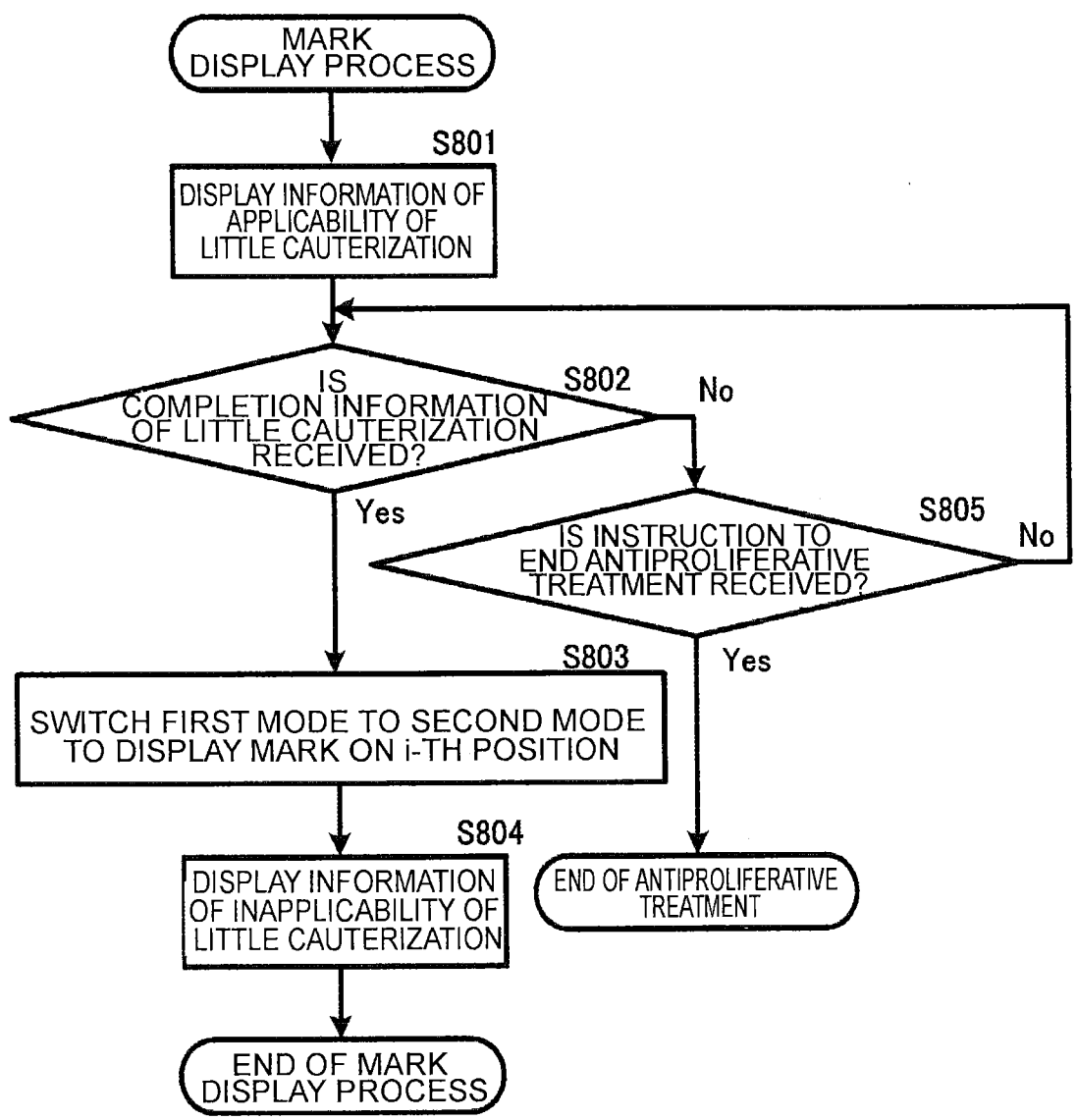
FIG. 19 is a flowchart of a mark display process in the first embodiment.

In the following, a description is given of the mark display process with reference to FIG. 19. FIG. 19 is a flowchart of the mark display process. As illustrated in FIG. 19, the display processor 18 displays information as to the applicability of little cauterization on the display unit 40 (step S801). The display processor 18 then determines whether information on the completion of little cauterization (completion information) has been received (step S802). Having determined that completion information has been received (Yes in step S802), the display processor 18 switches the first mode (circle illustrated in FIG. 11) to the second mode (double-circle illustrated in FIG. 11) to display the mark MK placed on the i-th position (step S803). Thus, cauterization sites that have already been cauterized and those yet to be cauterized can be visually perceived.

After that, the display processor 18 displays information as to the inapplicability of little cauterization on the display unit 40 (step S804). Having determined that completion information has not been received (No in step S802), the display processor 18 determines whether an instruction to end the antiproliferative treatment has been received (step S805). When the display processor 18 determines that an instruction to end the antiproliferative treatment has been received (Yes in step S805), the antiproliferative treatment is finished. If not (No in step S805), the process returns to step S802 of determining whether completion information has been received.

Second Embodiment

In the following, a description is given of a medical image diagnosis apparatus according to the second embodiment with reference to FIGS. 20 and 21. In the second embodiment, like elements as described in the first embodiment are designated by like reference numerals, and their description is not repeated. The differences are mainly described below.

In the first embodiment, the display processor 18 adjusts the scale to the tilt angle of the puncture needle and the position of the needle tip at real cauterization time to display it on the display unit 40. Whereby, in antiproliferative treatment, when moving the position of the needle tip by a predetermined distance for each little cauterization, the operator can refer to the scale indicating a predetermined interval that is equal to the predetermined distance. Thus, the operator can easily perform the antiproliferative treatment.

Figure 20:
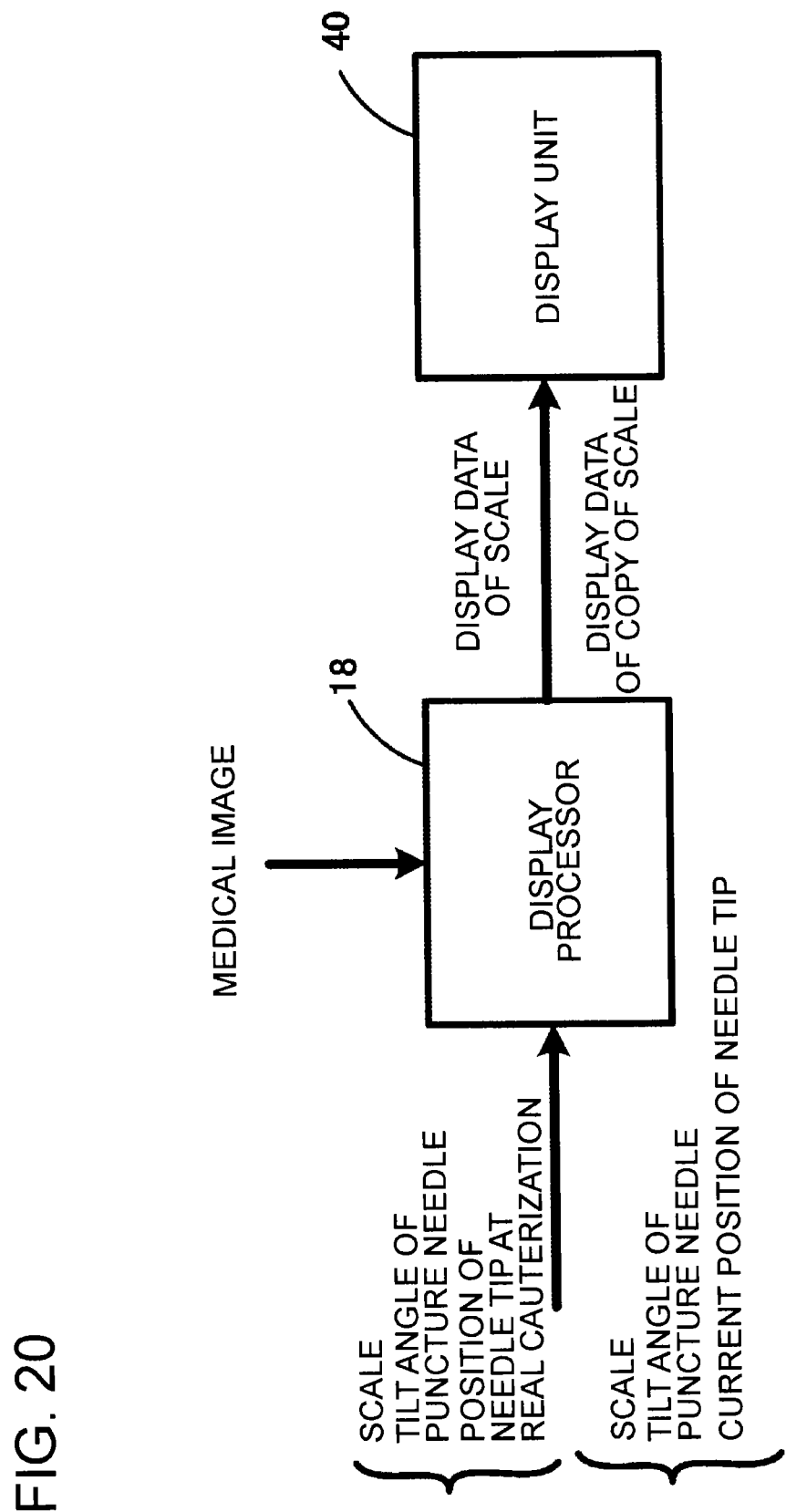
FIG. 20 is a functional block diagram of a display processor and the like according to a second embodiment.

FIG. 20 is a functional block diagram of a display processor and the like according to the second embodiment. As illustrated in FIG. 20, in the second embodiment, the display processor 18 retrieves the current position of the needle tip and the tilt angle of the puncture needle at real cauterization time from the memory 16. The display processor 18 displays, in addition to the scale, a copy of the scale adjusted to the current position of the needle tip and the tilt angle of the puncture needle on the display unit 40. This further facilitates antiproliferative treatment. Since the copy of the scale moves along with the position of the needle tip, the movement of the needle tip can be easily perceived. Moreover, in antiproliferative treatment, when the position of the needle tip moves a predetermined distance, the marks MK of the scale match those of the copy. Thus, the movement of the needle tip can be followed more easily.

Figure 21:
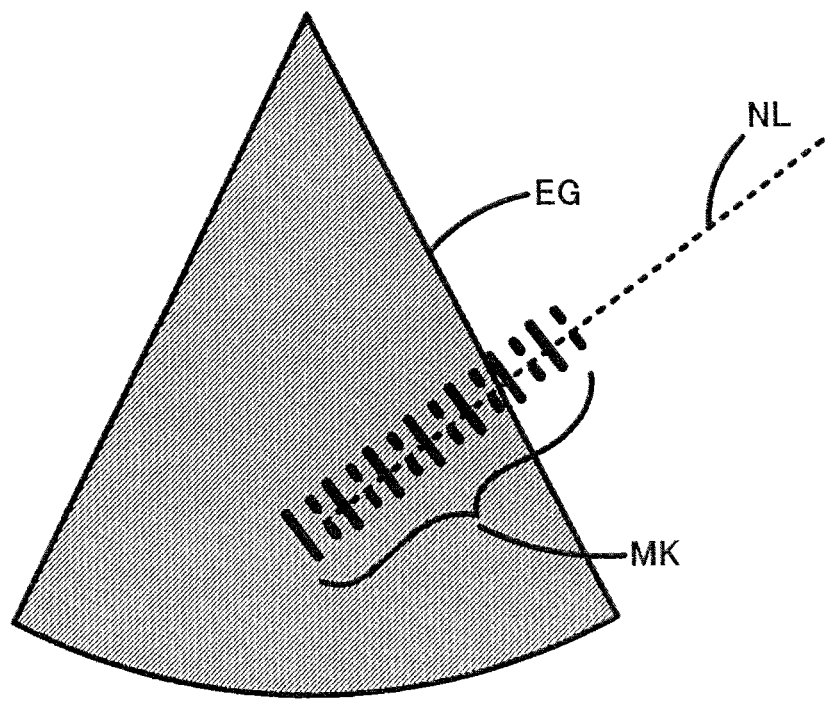
FIG. 21 is a schematic view of an example of display mode of a scale, illustrating the scale displayed according to the position of a needle tip at real cauterization time and a copy of the scale displayed according to the position of the needle tip that moves during the antiproliferative treatment time in the second embodiment.

FIG. 21 is a schematic view of the scale displayed according to the position of the needle tip at real cauterization time and a copy of the scale displayed according to the position of the needle tip that moves during antiproliferative treatment time. As illustrated in FIG. 21, the display processor 18 displays the scale adjusted to a real cauterization site, and also a copy of the scale represented by a dashed line, which shifts from the real cauterization site together with the position of the needle tip (indicated by the tip of the needle-stick guideline NL). FIG. 21 illustrates the difference or mismatch between the marks MK of the solid scale and those of the copy represented by a dashed line. With the display of the difference, the operator can visually check that the position of the needle tip has not yet moved a predetermined distance. Thus, the operator can follow the movement of the needle tip even more easily.

Third Embodiment

Figure 22:
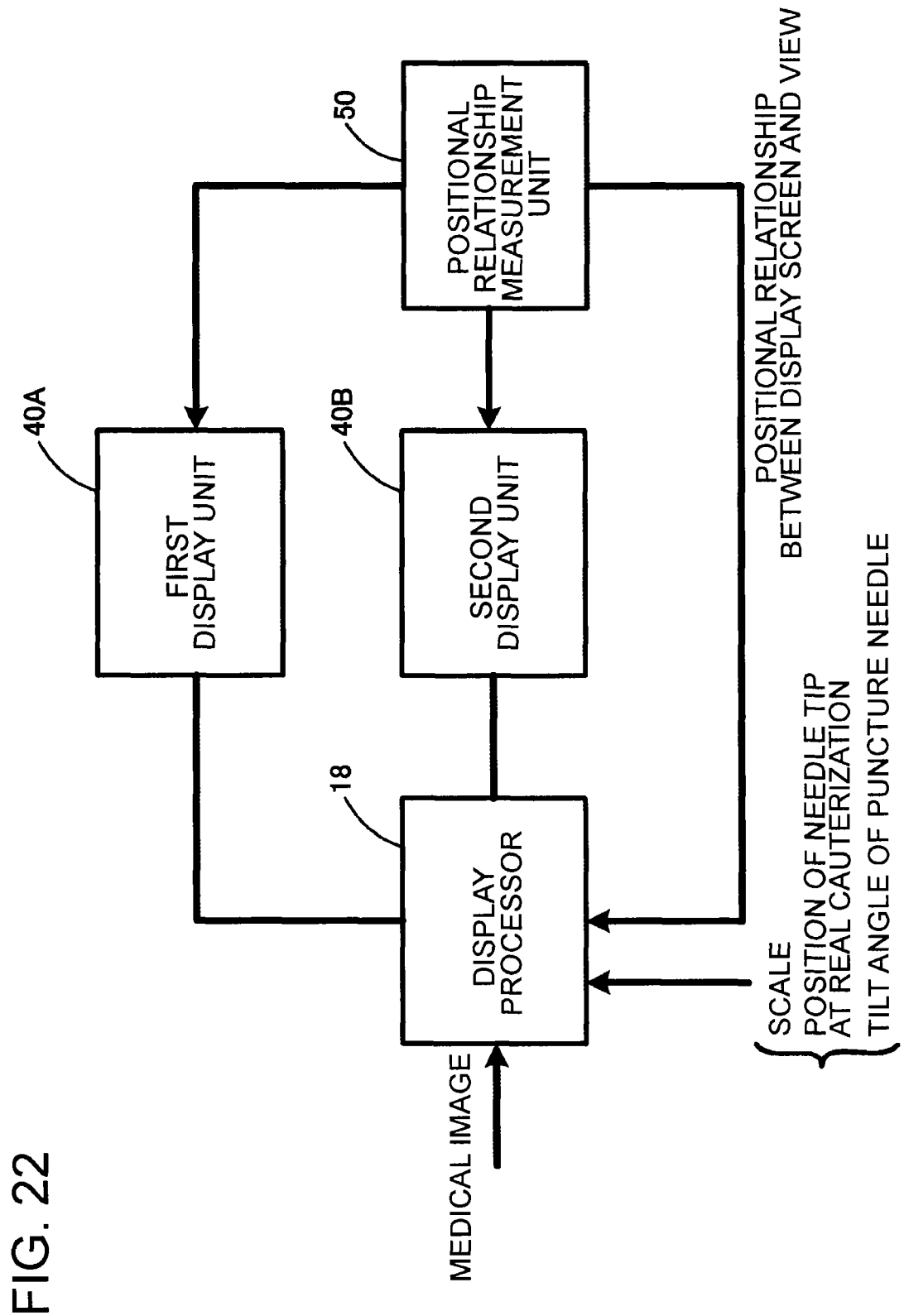
FIG. 22 is a functional block diagram of a display processor and the like according to a third embodiment.

In the following, a description is given of a medical image diagnosis apparatus according to the third embodiment with reference to FIG. 22. In the third embodiment, like elements as described in the first embodiment are designated by like reference numerals, and their description is not repeated. The differences are mainly described below.

In the first embodiment, the display processor 18 adjusts the scale to the tilt angle of the puncture needle and the position of the needle tip at real cauterization time to display it with a medical image on the display unit 40.

The scale and the medical image may be displayed on the same display unit 40, or may be displayed on different display units.

In the third embodiment, the display unit 40 includes a first display unit 40A and a second display unit 40B. The first display unit 40A includes a general display device. The second display unit 40B includes a wearable glass device that incorporates a display into an eyeglass. The display processor 18 displays a medical image including an image of the puncture needle on the first display unit 40A, and the scale and the needle-stick guideline NL on the second display unit 40B. During a puncture, it is required to adjust the scale and the needle-stick guideline NL displayed on the second display unit 40B to the position of the needle tip in the image of the puncture needle displayed on the first display unit 40A. To adjust the both, a positional relationship measurement unit 50 measures a positional relationship between the display screen of the first display unit 40A and a view on the second display unit 40B.

According to the result of the measurement by the positional relationship measurement unit 50, indicating that the view on the second display unit 40B matches the display screen of the first display unit 40A, the display processor 18 matches coordinates to display the medical image with coordinates to display the scale and the like. Thus, the display processor 18 displays the medical image including the image of the puncture needle on the first display unit 40A, and the scale and the needle-stick guideline NL on the second display unit 40B.

While the third embodiment describes that the display processor 18 displays the medical image on the first display unit 40A, and the scale and the like on the second display unit 40B, this is by way of example and not as limitation. The scale and the like may be displayed with the medical image on the display of the glass device.

In the above embodiments, the scale is adjusted to the position of the needle tip at real cauterization time. However, the scale is not necessarily adjusted to the position of the needle tip. The scale may be adjusted to the reference position of the puncture needle. The reference position may be specified by the operator. Besides, although the scale is described as being fixed after adjusted to the position of the needle tip, the position to which the scale is adjusted may be changed from the position of the needle tip at real cauterization time to a desired position.

In the above embodiments, an example is described in which, when one puncture needle is used in a puncture, the display processor 18 displays the scale to enable the operator to visually check little cauterization sites in antiproliferative treatment. However, a plurality of puncture needles may be used in a puncture. On such an occasion, the display processor 18 may display the scale for one of the puncture needles selected by the operator through the input unit 21 so that the operator can visually check little cauterization sites in antiproliferative treatment with respect to the selected needle.

In the above embodiments, the two-dimensional coordinates of the scale are adjusted to the two-dimensional coordinates of a medical image to display the scale with the medical image. However, this is not so limited. For example, the capturing part acquires three-dimensional coordinates of the medical image. When rotating the three-dimensional coordinates of the medical image for display, the display processor 18 may adjust the three-dimensional coordinates of the scale to the three-dimensional coordinates of the medical image to thereby display the scale with the medical image. This achieves three-dimensional display in which a mark MK placed nearer to the current position of the needle tip appears closer.

Upon providing the zoom in/out display of a medical image, the display processor 18 may display the scale zoomed in/out according to the zoom factor of the medical image. Besides, in the above embodiments, the display mode of the scale is switched between the first mode and the second mode to notify the operator of whether the position of the needle tip has moved a predetermined distance. The operator may be informed of this by color change, sound, or vibration. Alternatively, the operator may be informed through another device that he/she possesses.

In the above embodiments, while an ultrasonic diagnosis apparatus is described as an example of the medical image diagnosis apparatus, and the ultrasonic probe 20 is exemplified as the capturing part, they are not so limited. Other examples of the medical image diagnosis apparatus include an X-ray CT system. As an example of the capturing part of the X-ray CT system may be cited a scanning bed on which a subject lies. In this case, the second position and the third position are defined in the scanning bed.

Further, the position measurement system 300 is presented as an example of a measurement unit that measures the first position on the puncture needle and the second position on the ultrasonic probe 20. However, anything may be employed as the measurement unit as long as it is capable of measuring the three-dimensional coordinates of the first position and the second position, and the tilt angle of the ultrasonic probe 20.

The needle tip is described above as being brought in contact with the third position that is in a predetermined positional relationship with the second position. Needless to say, the needle tip may be brought in contact with the second position. At this time, the third position coincides with the second position.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis apparatus, comprising:
a capturing device configured to photograph a target site of a subject and a puncture needle inserted into the target site to capture a medical image;
a calculator configured to
perform measurements of a position of a sensor located at an opposite end from a needle tip of the puncture needle inserted into the target site and a tilt angle of the puncture needle, and
obtain a position of the needle tip based on results of the measurements and a needle length, which corresponds to a length of a straight line from the position of the sensor to the position of the needle tip, to acquire positional information of the puncture needle; and
a display processor configured to
arrange scales, which are graduated at predetermined intervals, along a guideline according to the position of the needle tip and the tilt angle of the puncture needle obtained when the puncture needle reaches a cauterization object in the target site, and display the guideline with the medical image.

2. The medical image diagnosis apparatus of claim 1, wherein the calculator is further configured to obtain the position of the needle tip as the reference position when the puncture needle reaches a cauterization object in the target site, and measure the tilt angle of the puncture needle when the puncture needle reaches the cauterization object, and the display processor is further configured to adjust the scales to the position of the needle tip and the tilt angle of the puncture needle to generate the guideline having the scales placed along the insertion route.

3. The medical image diagnosis apparatus of claim 2, further comprising a memory to store a predetermined relationship between a value representing an intensity of cauterization and each distance from the position of the needle tip during the cauterization to an insertion position, wherein the calculator is further configured to
obtain the insertion position where the puncture needle is inserted into skin of the subject based on a pixel value of the medical image; and
determine a particular intensity of cauterization with reference to the predetermined relationship, based on a distance from the obtained position of the needle tip to the insertion position.

4. The medical image diagnosis apparatus of claim 1, wherein the scales of the generated guideline are marks that are placed on a plurality of positions spaced at the predetermined intervals.

5. The medical image diagnosis apparatus of claim 1, wherein the medical image is displayed on a display device including a glass device that incorporates the display into an eyeglass, and the display processor is further configured to display the guideline with the medical image on the display.

6. The medical image diagnosis apparatus of claim 1, wherein the medical image is displayed on a display device including a first display device configured to display the medical image, and a second display device including a glass device that incorporates the display into an eyeglass, the calculator is further configured to measure a positional relationship between a display screen of the first display device and a view on the second display device, and when it is determined that the view on the second display device and the display screen of the first display device are in a predetermined positional relationship based on a result of measurement, the display processor is further configured to cause the guideline to be displayed on the display.

7. The medical image diagnosis apparatus of claim 1, wherein the calculator is further configured to sequentially obtain the position of the needle tip while the puncture needle is being removed, and the display processor is further configured to cause a copy of the scales to be displayed together with the scales and the medical image, the copy being adjusted to the position of the needle tip sequentially obtained and the tilt angle of the puncture needle.

8. The medical image diagnosis apparatus of claim 1, further comprising a memory to store the position of the needle tip at last cauterization, wherein the calculator is further configured to obtain the position of the needle tip while the puncture needle is being removed, and obtain a distance between the position of the needle tip stored in the memory and the obtained position of the needle tip, and determine whether the distance exceeds a predetermined distance, and the display processor is further configured to cause display of applicability information indicating that cauterization can be performed when the distance exceeds the predetermined distance.

9. The medical image diagnosis apparatus of claim 8, wherein, having been informed of completion of the cauterization after displaying the applicability information, the display processor is further configured to cause display of completion information indicating that the cauterization is completed.

10. The medical image diagnosis apparatus of claim 9, wherein the display processor is further configured to cause display marks placed on a plurality of positions provided at the predetermined intervals in distinguishable different modes to be displayed to provide the applicability information and the completion information.

11. The medical image diagnosis apparatus of claim 1, wherein the capturing device is configured to acquire three-dimensional coordinates of the medical image, and the display processor is further configured to, when rotating the three-dimensional coordinates of the medical image for display, adjust three-dimensional coordinates of the scales to the three-dimensional coordinates of the medical image.

12. The medical image diagnosis apparatus of claim 1, wherein the display processor is further configured to, when providing zoom in/out display of the medical image, cause display of the guideline zoomed in/out according to a zoom factor of the medical image.

* * * * *